(12) United States Patent
Schneeberger

(10) Patent No.: US 12,426,886 B2
(45) Date of Patent: Sep. 30, 2025

(54) ATRIAL APPENDAGE EXCLUDER

(71) Applicant: Eric William Schneeberger, Cincinnati, OH (US)

(72) Inventor: Eric William Schneeberger, Cincinnati, OH (US)

( * ) Notice: Subject to any disclaimer, the term of this patent is extended or adjusted under 35 U.S.C. 154(b) by 315 days.

(21) Appl. No.: 18/254,147

(22) PCT Filed: Nov. 23, 2021

(86) PCT No.: PCT/US2021/060569
§ 371 (c)(1),
(2) Date: May 23, 2023

(87) PCT Pub. No.: WO2022/109475
PCT Pub. Date: May 27, 2022

(65) Prior Publication Data
US 2024/0000458 A1    Jan. 4, 2024

Related U.S. Application Data

(60) Provisional application No. 63/117,144, filed on Nov. 23, 2020.

(51) Int. Cl.
*A61B 17/12* (2006.01)
*A61B 17/00* (2006.01)

(52) U.S. Cl.
CPC .. *A61B 17/12122* (2013.01); *A61B 17/12031* (2013.01); *A61B 17/12163* (2013.01); *A61B 2017/00588* (2013.01)

(58) Field of Classification Search
CPC ... A61B 17/12; A61B 17/122; A61B 17/1227; A61B 17/1327; A61B 17/1322
See application file for complete search history.

(56) References Cited

U.S. PATENT DOCUMENTS

| | | |
|---|---|---|
| 9,445,895 B2 | 9/2016 | Kreidler |
| 9,486,225 B2 | 11/2016 | Michler et al. |
| 9,808,253 B2 | 11/2017 | Li et al. |
| 9,826,980 B2 | 11/2017 | Figulla et al. |
| 9,861,370 B2 | 1/2018 | Clark et al. |
| 9,861,371 B2 | 1/2018 | Martin et al. |
| 9,883,867 B2 | 2/2018 | Martin et al. |
| 9,888,925 B2 | 2/2018 | Bertolero et al. |
| 9,901,350 B2 | 2/2018 | McGuckin, Jr. |

(Continued)

*Primary Examiner* — Darwin P Erezo
*Assistant Examiner* — Raihan R Khandker
(74) *Attorney, Agent, or Firm* — Jenei LLC

(57) ABSTRACT

An occlusion clip is disclosed herein. The occlusion clip comprises a resilient base strip including a plurality of base strip segments defining a hexagonal profile that represents an open state of the occlusion clip. A plurality of housing segments is provided on each of the base strip segments. A core element is disposed and extends within the housing segments defining a half of the hexagonal profile, wherein the core element is configured for linear movement within the housing segments. An actuator cable extends from each of the core elements, wherein in an actuated state, the core element is pulled via the actuator cable, and the pulling facilitates relative movement between the housing segments and the core elements causing the core element to make the housing segments collinear, thereby defining a closed configuration of the occlusion clip.

19 Claims, 33 Drawing Sheets

(56) References Cited

U.S. PATENT DOCUMENTS

| | | |
|---|---|---|
| 9,901,351 B2 | 2/2018 | Winkler et al. |
| 9,901,352 B2 | 2/2018 | Fago et al. |
| 9,913,652 B2 | 3/2018 | Bridgeman et al. |
| 9,936,956 B2 | 4/2018 | Fung et al. |
| 10,076,335 B2 | 9/2018 | Zaver et al. |
| 10,098,640 B2 | 10/2018 | Bertolero et al. |
| 10,143,456 B2 | 12/2018 | Javois |
| 10,143,475 B2 | 12/2018 | Ibrahim et al. |
| 10,166,024 B2 | 1/2019 | Williamson, IV et al. |
| 10,182,824 B2 | 1/2019 | Manti et al. |
| 10,201,352 B2 | 2/2019 | Fago et al. |
| 10,238,398 B2 | 3/2019 | Hughett, Sr. et al. |
| 10,258,343 B2 | 4/2019 | Li et al. |
| 10,278,704 B2 | 5/2019 | Kiser et al. |
| 10,285,712 B2 | 5/2019 | Cosgrove, III et al. |
| 10,314,585 B2 | 6/2019 | Williamson, IV et al. |
| 10,314,594 B2 | 6/2019 | de Canniere |
| 10,349,948 B2 | 7/2019 | Rogowski et al. |
| 10,405,866 B2 | 9/2019 | Chakraborty et al. |
| 10,426,475 B2 | 10/2019 | Privitera et al. |
| 10,426,488 B2 | 10/2019 | Michler et al. |
| 10,524,791 B2 | 1/2020 | Bertolero et al. |
| 10,531,878 B2 | 1/2020 | Slaughter et al. |
| 10,548,579 B2 | 2/2020 | Turkington et al. |
| 10,575,851 B2 | 3/2020 | Rogers et al. |
| 10,603,020 B2 | 3/2020 | Rudman et al. |
| 10,610,208 B2 | 4/2020 | Whayne et al. |
| 10,617,425 B2 | 4/2020 | Kaplan et al. |
| 10,624,648 B2 | 4/2020 | Li et al. |
| 10,631,874 B2 | 4/2020 | Martin et al. |
| 10,660,649 B2 | 5/2020 | Ad |
| 10,667,896 B2 | 6/2020 | Delaney, Jr. et al. |
| 10,709,454 B2 | 7/2020 | Li et al. |
| 10,716,571 B2 | 7/2020 | Fung et al. |
| 10,729,447 B2 | 8/2020 | Shimizu et al. |
| 10,750,936 B2 | 8/2020 | Okazaki et al. |
| 10,751,158 B2 | 8/2020 | Sutton et al. |
| 10,758,240 B2 | 9/2020 | Edmiston et al. |
| 10,758,241 B1 | 9/2020 | Lashinski et al. |
| 10,758,243 B2 | 9/2020 | Salas |
| 10,765,416 B2 | 9/2020 | Li |
| 2006/0020271 A1 | 1/2006 | Stewart et al. |
| 2007/0213747 A1* | 9/2007 | Monassevitch ...... A61B 17/122 606/151 |
| 2008/0039879 A1 | 2/2008 | Chin et al. |
| 2011/0009853 A1* | 1/2011 | Bertolero ............. A61B 17/083 606/14 |
| 2013/0253550 A1* | 9/2013 | Beisel ................. A61B 17/1114 606/153 |
| 2016/0100844 A1 | 4/2016 | Li et al. |
| 2016/0166242 A1 | 6/2016 | Krishnan |
| 2016/0235412 A1 | 8/2016 | Liddicoat et al. |
| 2016/0262767 A1 | 9/2016 | Miles et al. |
| 2016/0270784 A1 | 9/2016 | Wheeler et al. |
| 2018/0132857 A1 | 5/2018 | Fago et al. |
| 2018/0199944 A1 | 7/2018 | Hughett, Sr. et al. |
| 2018/0221126 A1* | 8/2018 | Igov ................... A61B 17/1285 |
| 2018/0310936 A9 | 11/2018 | Bertolero et al. |
| 2018/0317922 A1 | 11/2018 | Winkler et al. |
| 2019/0117229 A1 | 4/2019 | Ibrahim et al. |
| 2019/0142428 A1 | 5/2019 | Widenhouse et al. |
| 2019/0216465 A1 | 7/2019 | Hughett, Sr. et al. |
| 2019/0231356 A1 | 8/2019 | Deville et al. |
| 2019/0357912 A1 | 11/2019 | Privitera et al. |
| 2020/0100789 A1 | 4/2020 | Bertolero et al. |

\* cited by examiner

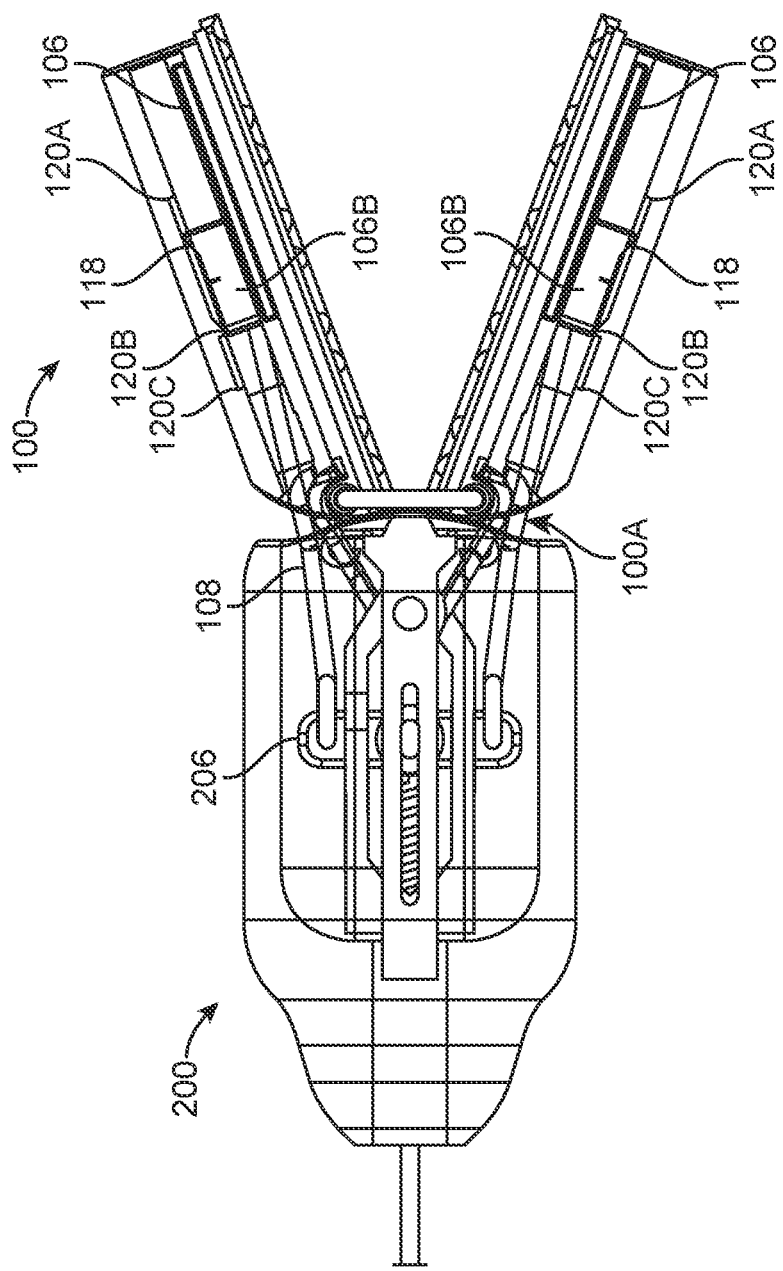

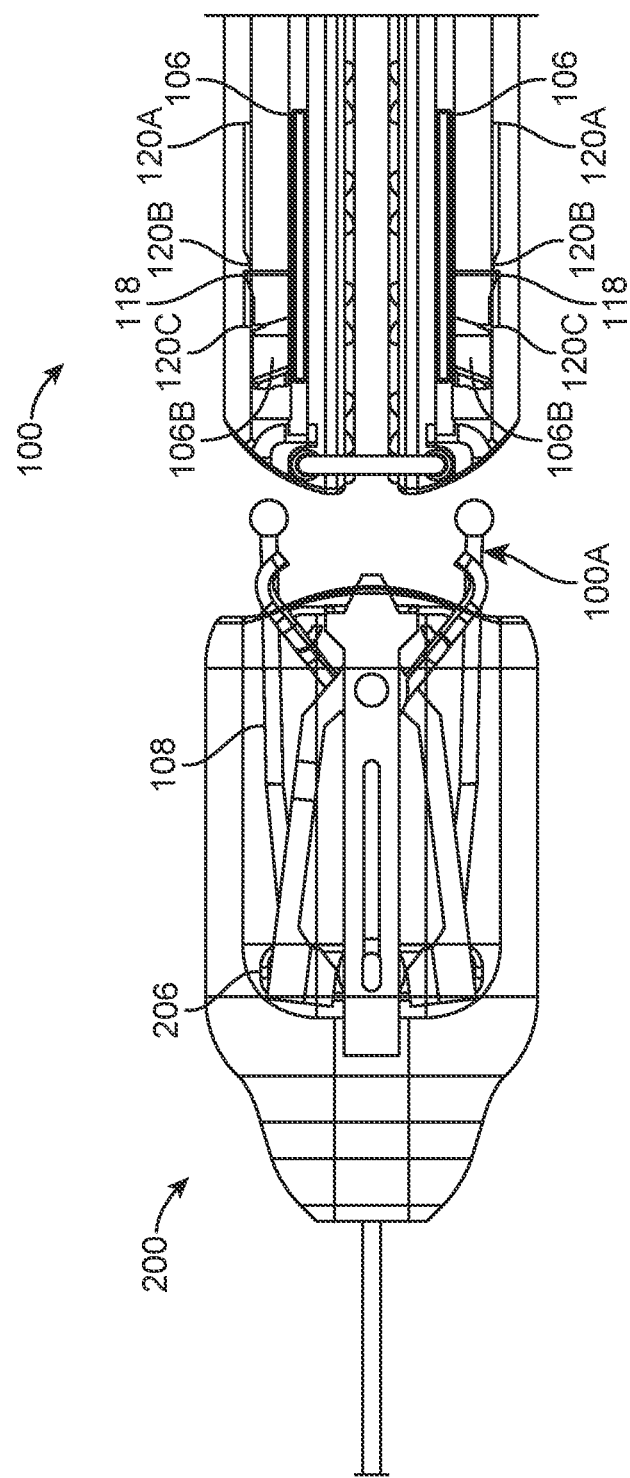

ATRIAL APPENDAGE EXCLUDER

CROSS-REFERENCE TO RELATED APPLICATIONS

The present Application is a National Stage application filed under 35 U.S.C. § 371 of International Application No. PCT/US21/60569, entitled "ATRIAL APPENDAGE EXCLUDER" and filed on Nov. 23, 2021, which claims the benefit of U.S. Provisional Application Ser. No. 63/117,144 entitled "ATRIAL APPENDAGE EXCLUDER" filed Nov. 23, 2020, which are hereby expressly incorporated by reference herein to form part of the present disclosure.

TECHNICAL FIELD

The present disclosure relates generally to an occlusion clip, and more particularly, to an occlusion clip. The present invention also provides for an implantable occlusion clip that may be used to occlude the left atrial appendage.

BACKGROUND

In 2018, it was found that one in six deaths associated with cardiovascular disorders were caused due to a stroke. Those who survive a stroke may fall prey to disabilities. One of the most common reasons contributing to occurrence of a stroke emanating from the heart is thrombus formation due to atrial fibrillation. Atrial fibrillation refers to an irregular, often rapid heart rate that commonly causes poor blood flow. An after effect of the irregular chaotic heart beats is that it produces lower cardiac output and irregular and turbulent blood flow in the vascular system. To this end, a patient suffering from atrial fibrillation may have to be put on a specifically designed pharmaceutical regimen to reduce the risks associated with atrial fibrillation.

An effect of the atrial fibrillation, as mentioned above, is the development of atrial thrombus, which typically causes the clot to occur in the left atrial appendage (LAA) of the heart. The LAA is an appendage that extends from a lateral wall of the left atrium of the heart and has a small finger like shape that defines the cavity therein. In a normal heartbeat cycle, the LAA contracts with the entirety of the left atrium, thereby keeping the blood pumping and preventing the stagnation of the blood therein. However, in patients suffering from atrial fibrillation, the left atrium and LAA fail to contract due to discordant electrical signals associated with atrial fibrillation. As such, the pumping of the blood out of the left atrium is impacted resulting blood stagnation therein, subsequently leading to thrombus formation, which is an undesirable outcome. It has been observed that elimination or containment of the thrombus formed within the LAA in patients due to atrial fibrillation significantly reduces the incidents of stroke.

As mentioned before, patients having thrombus formation have to be put on specifically designed pharmaceutical regimen, which may include administration of warfarin or other blood thinners. However, it has been observed that the usage of the aforementioned drugs has been suboptimal due to serious side effects of the medications accompanied by the lack of patient compliance in actually taking the medication as per the regimen in the correct quantity. To this end, invasive surgeries for occluding the LAA have been developed.

As such, there is felt a need of an occlusion device for occluding the LAA in a way that is minimally invasive and can be used with conventionally available ablation devices for occluding a targeted tissue in the body, one example of which is the LAA.

SUMMARY

Devices, tools, and methods for occluding fluid flow between two walls of tissue in a patient are provided. Two walls of tissue are compressed together with sufficient compressive force to prevent fluid flow between the two walls, while ensuring that the compressive force is not so great as to cause cutting of the tissue. Device and tools are provided for occluding fluid flow between two walls of tissue using minimally invasive surgical techniques, such as in reduced-access surgical sites. Devices, tools, and methods are provided for occluding an atrial appendage.

In at least one embodiment, a device for occluding fluid flow between two walls of tissue in a patient includes a base configured to apply compressive force against a first of the two walls; and at least one opposing member configured to apply compressive force against a second of the two walls upon installing the device, wherein, when installed, the base and the at least one opposing member compress the two walls therebetween, and a gap of predetermined dimension is established between the base and the at least one opposing member to sufficiently compress the two walls to occlude fluid flow therebetween, while preventing an establishment of a compression force that meets or exceeds a compression force to cause tissue laceration.

In at least one embodiment, a device for occluding fluid flow between two walls of tissue in a patient includes a clip comprising having sufficient length to traverse an entire width of the tissue walls defining a passageway through which fluid flow occurs, wherein, upon deployment to compress the tissue walls with sufficient force to occlude fluid flow therebetween, while preventing an establishment of a compression force that meets or exceeds a compression force to cause tissue laceration.

In at least one embodiment, a device for occluding fluid flow between two walls of tissue in a patient and a tool for installing the device are provided. An assembly for performing an occlusion of fluid flow between two walls of tissue in a patient is provided, including a device configured to maintain the two walls under sufficient compression to prevent fluid flow therebetween; and a tool configured to guide installation of the device into a final configuration where the device maintains the two walls under sufficient compression.

The present disclosure discloses an occlusion clip. The occlusion clip comprises a resilient base strip including a plurality of base strip segments defining a hexagonal profile that represents an open state of the occlusion clip. The vertices of the hexagonal profile are defined by live hinges formed due to a resilient nature of the base strip. The occlusion clip further comprises a plurality of housing segments, wherein one housing segment is provided on each of the base strip segments. A pair of core elements is disposed and extends within the plurality of housing segments defining a half of the hexagonal profile. The core element is configured for linear movement within the housing segments. An actuator cable extends from each of the core elements, wherein in an actuated state, the core element is pulled via the actuator cable, and the pulling facilitates relative movement between the housing segments and the core elements causing the core element to straighten out the live hinges to make the housing segments collinear, thereby defining a closed configuration of the occlusion clip.

In a non-limiting alternative embodiment, the base strip and the core elements are made of a resilient material.

In a non-limiting alternative embodiment, each of the core elements includes a base and a plurality of tabs configured on the base, wherein the plurality of tabs has a shape complementary to a shape of an inner periphery of the housing segments, wherein the housing segments have a hollow configuration.

In a non-limiting alternative embodiment, the plurality of tabs and the inner periphery of the housing segments define a trapezoidal shape such that the core element is allowed guided movement within the housing segments by virtue of the plurality of tabs.

In a non-limiting alternative embodiment, a first tab of the plurality of tabs is configured to receive the actuator cable securely until the actuator cable is pulled out of the occlusion clip subsequent to the closing of the occlusion clip.

In a non-limiting alternative embodiment, the first tab defines a rigid section and a winged section.

In a non-limiting alternative embodiment, the winged section comprises a pair of wings configured for extending hingedly and resiliently from laterally opposite ends of rigid section.

In a non-limiting alternative embodiment, the winged section, including a base of the winged section and the pair of wings of the winged section, define a receiving socket in a closed state of the pair of wings for securely receiving a ball of the actuator cable that facilitates the pulling action of the core elements.

In a non-limiting alternative embodiment, the ball of the actuator cable is configured to be released from the receiving socket subsequent to an opening of the pair of wings via hinged extension thereof.

In a non-limiting alternative embodiment, the first tab is housed within a first housing segment of the plurality of housing segments. The first tab includes a locking protrusion for facilitating linear movement of the first tab guided in a keyway defined on an inner operative top surface of the first housing segment, wherein the keyway is defined between a pair of spaced apart notches. A first notch of the pair of notches is a back out preventer notch that allows abutment of the locking protrusion formed on the first tab for maintaining a position of the core element within the plurality of housing segments when the occlusion clip is in its open state. A second notch is spaced apart from the first notch and has a shape complementary to that of the locking protrusion. The second notch is configured to allow abutment of the locking protrusion thereon. A distance traveled by the first tab between the first notch and the second notch represents a first stage of a closure procedure of the occlusion clip, wherein in the first stage, the occlusion clip is openable subsequent to being closed by maneuvering the actuator cables to linearly move the core element backwards and forwards between the first notch and the second notch.

In a non-limiting alternative embodiment, the clip further comprises a third notch spaced apart from the second notch, wherein a distance traveled by the first tab between the second notch and the third notch represents a second stage of the closure procedure of the occlusion clip.

In a non-limiting alternative embodiment, the first housing element includes a locking cavity configured between the second notch and an operative end of the first housing element for accommodating therein the spread opened pair of wings after the first tab is pulled beyond the second notch.

In a non-limiting alternative embodiment, the occlusion clip further comprises a clip opener for reopening the occlusion clip after the occlusion clip is closed. The clip opener comprises a first block to be inserted within a housing segment adjacent a distal end of the occlusion clip. A spring is coupled to a rear end of the first block. A block coupled is to the free end of the spring, wherein the tab and the spring are configured to be accommodated inside the slot of the housing segment, and the block protrudes out of the housing segment. The block is configured to be actuated and snap fit into the slot of the housing segment, thereby causing the live hinges of the base strip to bend and change the state of the occlusion clip from the closed state to the open state.

In a non-limiting alternative embodiment, the occlusion clip further comprises a resilient barrier disposed operatively between adjacent housing segments, wherein the resilient barrier prevents an entry of surrounding tissue in a pinch zone formed between the housing segments in the open state of the occlusion clip.

In a non-limiting alternative embodiment, the resilient barrier is configured to be accommodated in slots configured on the housing segments, when the occlusion clip is in the closed state and the housing segments are collinear.

In a non-limiting alternative embodiment, the resilient barrier is one of a resilient sheet and a plurality of spaced apart bands.

The present disclosure includes, inter alia, medical devices and related methods, and, more specifically, devices for manipulating and/or applying traction to anatomical structures, such as a left atrial appendage of a heart, and related methods. Some example embodiments according to at least some aspects of the present disclosure may be particularly useful in connection with left atrial appendage occlusion procedures, such as to treat cardiac arrhythmias like atrial fibrillation, for the reasons discussed herein and the patent references incorporated by reference herein.

The above summary contains simplifications, generalizations and omissions of detail and is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION OF EXAMPLE EMBODIMENTS

Figure 1:
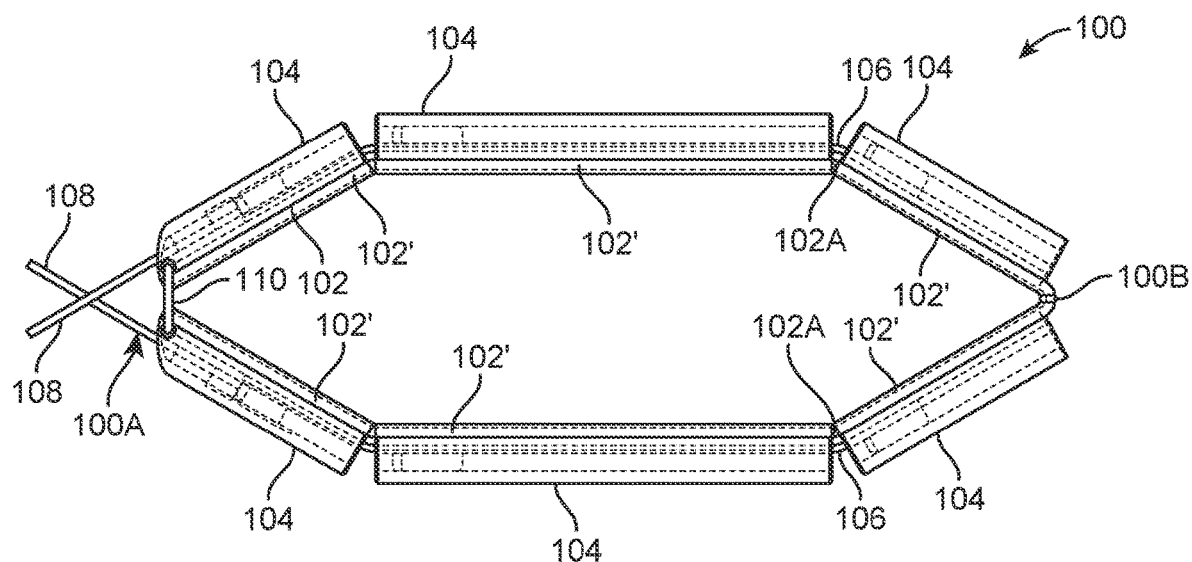
FIG. 1 and FIG. 2 exemplarily illustrate different views of an occlusion clip in an open state thereof, according to an embodiment of the present disclosure.

Atrial appendage management, and particularly left atrial appendage (LAA) management, is a critical part of the surgical treatment of atrial fibrillation. When using a minimally invasive approach (e.g., where surgical access is provided by thoracoscopy, mini-thoracotomy or the like), there is a high risk of complications such as bleeding, when using contemporary atrial appendage management, as noted above. Further, exposure and access to the base of the atrial appendage to be treated is limited by the reduced-access surgical site. The present invention provides devices, tools assemblies and methods for ligating or occluding an atrial appendage, which ligation or occlusion may be performed while the heart continues to beat, and wherein such ligation or occlusion methods may be performed using a minimally invasive approach. Such procedures may be performed solely from a thoracotomy in the left chest, or may be performed from ports placed in the left chest, or from a small sub-xyphoid opening, for example, if desired by the surgeon performing the procedure. For example, the opening through which the devices of the present invention may be inserted may be, a port or trocar commonly used in endoscopic surgical procedures. Particular locations in which small incisions may be made through which to deliver a device to perform atrial appendage ligation include, but are not limited to the left third or fourth intercostal space, or a subxyphoid location.

Described herein are various methods, assemblies, tools and devices for clamping tissue, particularly cardiac tissue. In one aspect, an assembly for delivering an implantable occlusion device includes an implantable occlusion device and an elongate shaft. The implantable occlusion device can extend from a distal portion of the shaft such that the combined device and shaft have a low-profile configuration. In use, this low-profile configuration permits implantation of the device with minimal patient trauma. In another aspect, the low-profile configuration of the assembly permits implantation via a subxyphoid approach to the left atrial appendage. The assembly can further comprise a movable connection between the shaft and device to allow at least a portion of the device to move relative to at least a portion of the shaft. In one aspect, the movable connection allows the device to move from a low-profile insertion configuration to a clamping configuration and/or to a device implantation configuration. Additionally, the assembly can include a detachable connection that permits all or a portion of the device to detach from the shaft, so that the device can be detached and implanted after clamping tissue.

In at least one embodiment, the implantable occlusion device is configured for clamping at least a portion of the left atrial appendage. For example, the device can be formed in a size and shape commensurate with the left atrial appendage and the body cavity in which the left atrial appendage is located. For example, the device can comprise a clip. The device can include at least two opposable clamping members and a locking mechanism for fixing the opposable clamping members relative to one another. In one aspect, the space between the two opposable clamping members, when fixed via the locking mechanism, is sized and shaped to receive a portion of the left atrial appendage. The tools described herein enable delivery, e.g., insertion and implantation, of a device via minimally invasive procedures. However, while the implantable occlusion device is described herein with respect to clamping the left atrial appendage, one skilled in the art will appreciate that the assemblies, tools, methods, and devices described herein can be configured for clamping other anatomical features.

Figure 2:
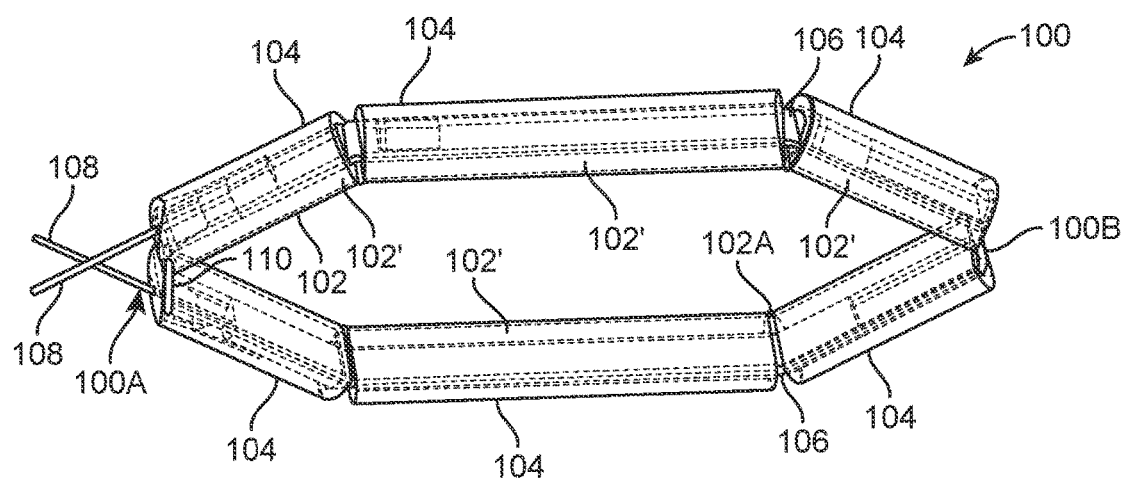
Figure 3A:
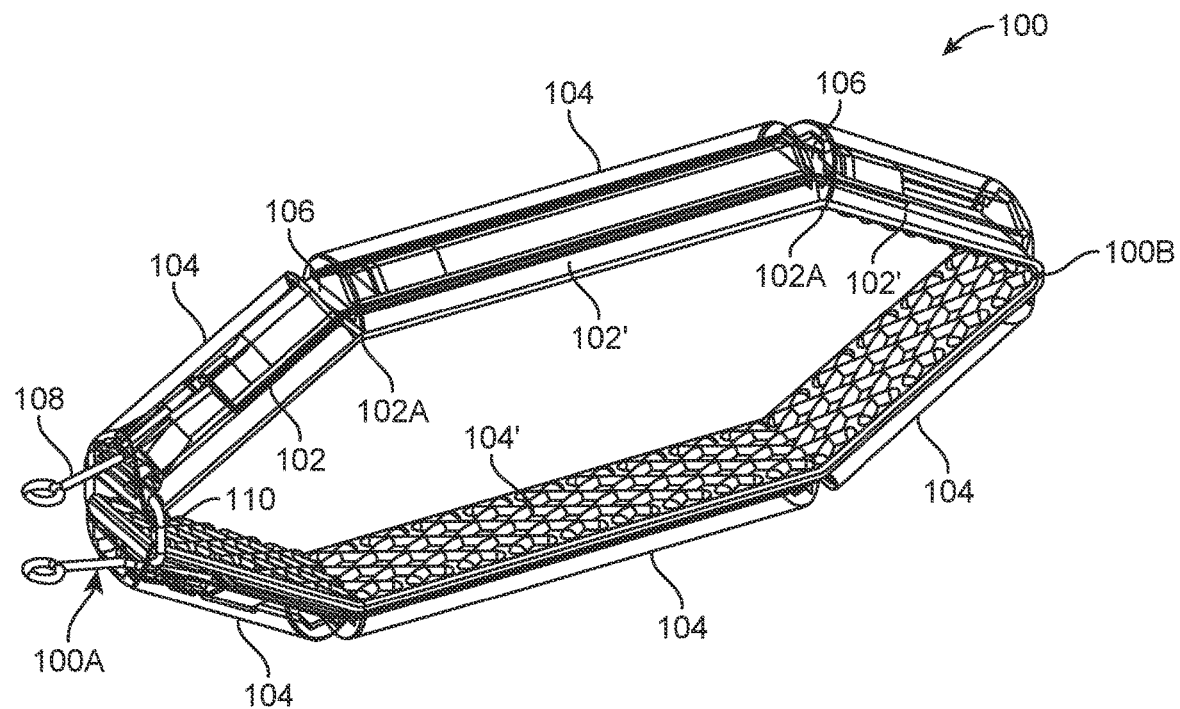
FIG. 3A and FIG. 3B exemplarily illustrate different views of an occlusion clip in the open state and closed state thereof, according to an embodiment of the present disclosure.
Figure 3B:
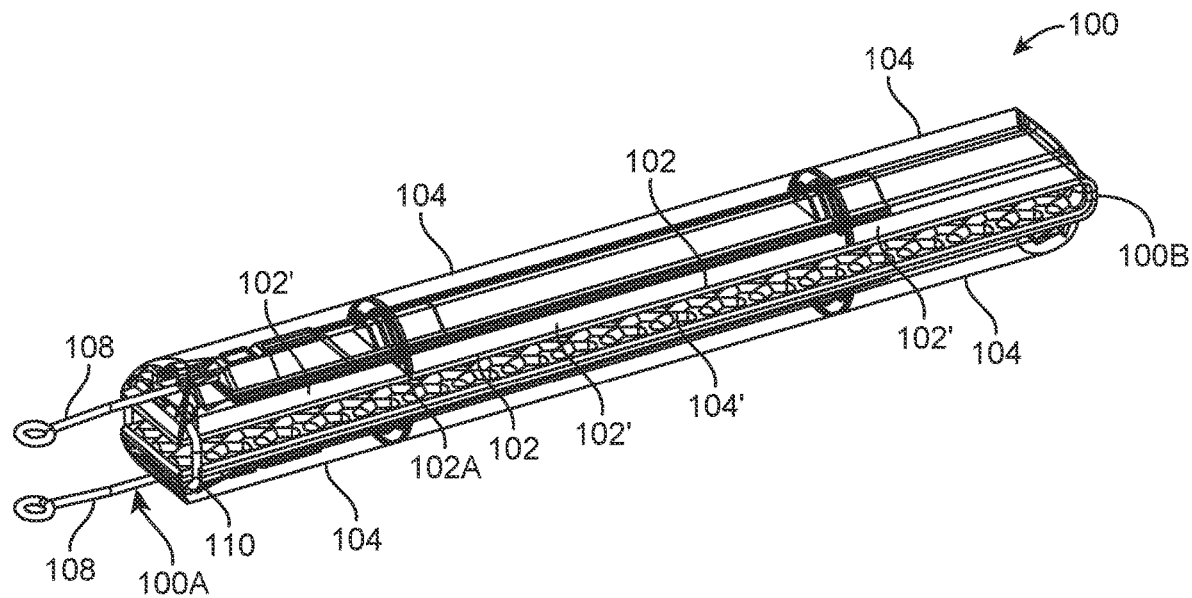

FIG. 1 and FIG. 2 exemplarily illustrate different views of an occlusion clip 100 in an open state thereof, according to an embodiment of the present disclosure. FIG. 3A and FIG. 3B exemplarily illustrate different views of an occlusion clip in the open state and closed state thereof, according to an embodiment of the present disclosure. Referring to FIG. 1 through FIG. 3B, the occlusion clip 100 has a proximal end 100A and a distal end 100B. The occlusion clip 100 comprises a base strip 102. The base strip 102 comprises a plurality of base strip segments 102'. The base strip 102 is made of a resilient material and looped into base strip segments 102' to form a hexagonal profile that represents an open state of the occlusion clip 100, in accordance with an embodiment of the present disclosure. In accordance with an embodiment of the present disclosure, the vertices of the hexagonal profile of the occlusion clip 100 form live hinges 102A due to the resilient nature of the base strip material.

The occlusion clip 100 further comprises a plurality of housing segments 104. More specifically, a housing segment 104 is provided on each of the base strip segment 102', in accordance with an embodiment of the present disclosure. In one embodiment, the base strip 102 and the housing segments 104 may be manufactured as a single component by methods, for example and not limited to, 3D printing. In another embodiment, the housing segments 104 and the base strip 102 may be manufactured as discreet components that may subsequently be assembled together. As seen in FIG. 1 and FIG. 2, the housing segments 104 are assembled over the base strip 102, wherein in one example, this assembly may be done by just sliding the housing segments 104 over the base strip 102. In another embodiment, the base strip 102 (slide) is moveable within the housing segments 104. Furthermore, as in the case of the clip embodiments described herein, the housing of the clip 104 is formed to not present or have any sharp edges or corners that could potentially cause damage to tissue within the patient's body. Each edge and corner of the clip strut body is rounded, curved, and/or beveled to create smooth or blunted surfaces.

The occlusion clip 100 further comprises a pair of core elements 106 disposed and extending within the plurality of housing segments 104 defining a half of the hexagonal profile. A half of hexagonal profile, in accordance with the present disclosure, refers to the one half of the hexagon formed on each side of an imaginary line passing through the proximal end 100A and the distal end 100B. More specifically, one core element 106 extends through three housing segments 104 that define each half of the hexagonal profile of the occlusion clip 100. The core element 106 is configured for linear movement within the housing segments 104. The construction and different features of the core element 106 are described in the subsequent sections of the present disclosure.

The occlusion clip 100 further comprises an actuator cable 108 that extends from each of the core elements 106, wherein in an actuated state, the core element 106 is pulled via the actuator cable 108, and the pulling facilitates relative movement between the housing segments 104 and the core elements 106 causing the core element 106 to straighten out the live hinges 102A to make the housing segments 104 collinear, thereby defining a closed configuration of the occlusion clip 100. The construction and operation of the actuator cable are described in the subsequent sections of the present disclosure.

The occlusion clip 100 further comprises a holding ring 110. The holding ring 110 is a resilient ring that holds together the free ends of the hexagonally looped base strip 102. An advantageous aspect of the holding ring 110, apart from holding the free ends of the hexagonally looped base strip 102, is that if the application of the occlusion clip 100 on the targeted tissue is not optimally executed or needs to be reopened and reapplied, the holding ring 110 may be cut to open up the free ends of the hexagonally looped base strip 102.

Referring to FIG. 3A, the occlusion clip 100 includes gripper formations 104' configured on the operative bottom surfaces of the housing segments 104 that are to be interfaced with the targeted tissue area while the occlusion clip is being applied thereon. The gripper formations 104' facilitate a secure application of the occlusion clip 100 on the targeted tissue area.

In one or more embodiments, the occlusion clip 100 can be manufactured in a variety of sizes for use with patients of different ages and/or physical sizes. One of ordinary skill in the art could determine the appropriate size of occlusion clip 100 for a particular patient by measuring the base of the appendage and applying standard diagnostic criteria well known in the medical and surgical arts. Occlusion clip 100 can be made of surgical grade materials including metals, polymers, ceramics, composites, and combinations thereof, including degradable biomaterials, bioceramics, biocomposites, biodegradable metal alloys such as, for example, polydioxanone and other biodegradable polymers, polyetheretherketone, liquid-crystal polymer, polymethyl-methacrylate, epoxy, titanium, stainless steel, chromium-cobalt alloy, nickel-titanium alloy or other metals or alloys.

Occlusion clip 100 can also be formed from any sufficiently rigid type of material that can be subjected to mechanical forces sufficient to insert the assembly into the body (i.e., pushing, pulling and/or twisting along an axis) and to open and close occlusion clip 100. Occlusion clip 100 can also be fabricated from materials designed to withstand sterilization by radiation, conventional autoclaving at high temperature and pressure, or other similar procedures for sterilization of surgical tools, instruments, sutures, or other medical implements intended for use inside the body cavity. Occlusion clip 100 can also be fabricated from materials designed to withstand sterilization which can then undergo slow hydrolysis by the body and thus be totally absorbed after the occluded appendage has been resorbed.

FIG. 4A through FIG. 6 illustrate different views of the occlusion clip 100 in a closed state thereof, according to an embodiment of the present disclosure. The closed state of the occlusion clip 100 is achieved by pulling the actuator cables 108 backwards. In the present disclosure, backwards refers to the direction pointing towards the left side in FIG. 1 and FIG. 3, and forward refers to the direction pointing towards the right side in FIG. 1 and FIG. 3.

Figure 4A:
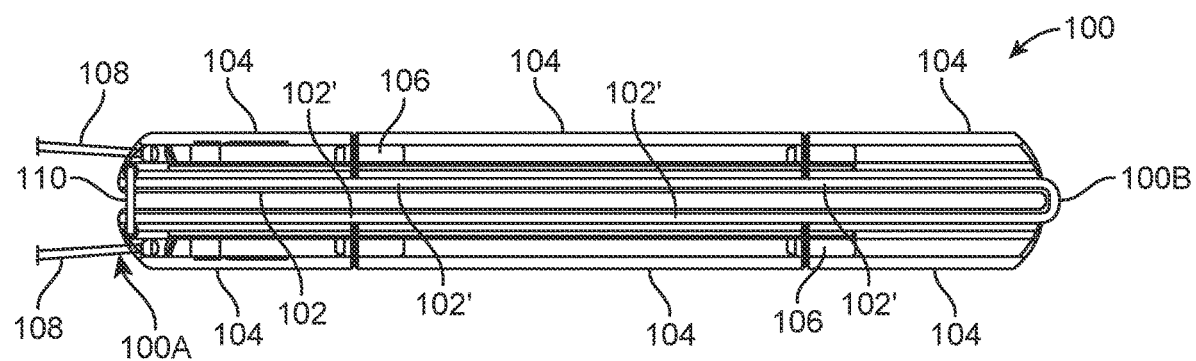
FIG. 4A through FIG. 6 illustrate different views of the occlusion clip in a closed state thereof, according to an embodiment of the present disclosure.
Figure 4B:
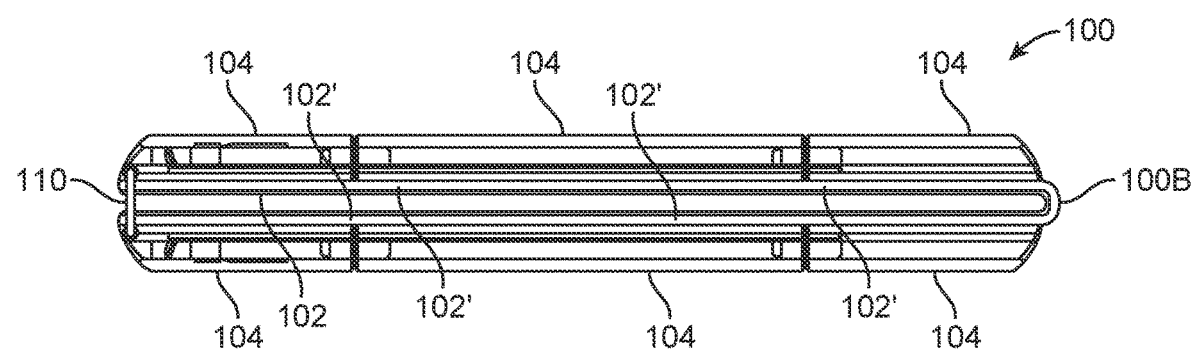

FIG. 4A depicts the view of the occlusion clip 100 just prior to complete closing of the clip 100, while FIG. 4B depicts the view of the occlusion clip 100 when the occlusion clip 100 is completely closed. As seen in FIG. 4B, on complete closure of the occlusion clip 100, the actuator cables 108 are released from the core elements 106. In accordance with one embodiment of the present disclosure, the relative movement between the housing segments 104 and the core elements 106 causing the core element 106 to straighten out the live hinges 102A to make the housing segments 104 collinear, thereby defining a closed configuration of the occlusion clip 100.

It is to be noted that the closure of the occlusion clip 100 is facilitated in two stages. In the first stage, the occlusion clip 100 is closed as seen in FIG. 4A but the surgeon still retains the control on reopening the clip 100 if the surgeon is not satisfied with the positioning of the clip 100 at the targeted tissue area. In this stage, the reopening of the clip 100 may be facilitated by manipulating the actuator cables 108. For example, if in the first stage of clip application, the surgeon feels that the clip placement is not optimal, the actuator cables 108 may be manipulated to apply a load on the core elements 106 in the forward direction.

The second stage of clip application may be the trigger stage. In the second stage, the surgeon may apply the clip 100 at the targeted tissue area by using a trigger mechanism that allows the actuator cables 108 to displace the core elements 106 in their final locked positions, wherein after the core elements 106 assume the final locked positions, the actuator cables 108 are disengaged from the core elements 106. The final locked position of the core elements 106 may be observed in FIG. 4B. As seen in FIG. 4B, the core elements 106 are shifted increasingly backwards relative of the position of the core elements 106 depicted in FIG. 4A.

Figure 5:
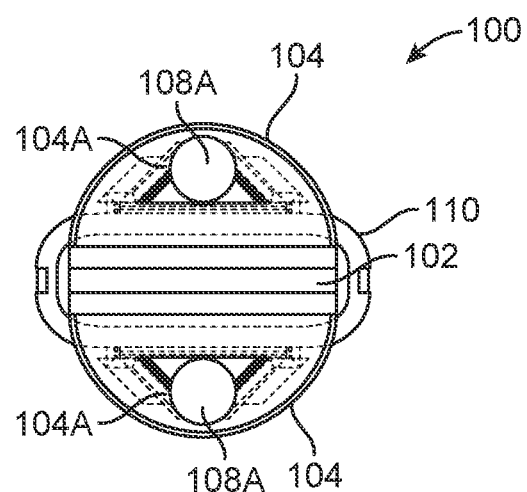
Figure 6:
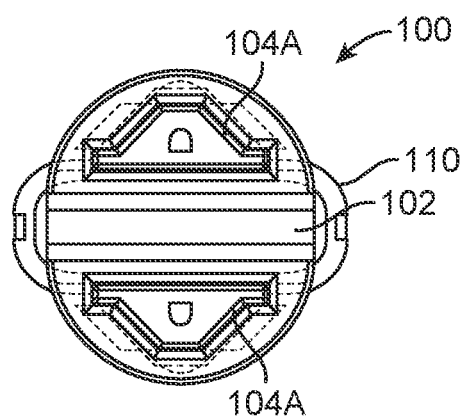

FIG. 5 and FIG. 6 depict side views of the occlusion clip 100, in accordance with an embodiment of the present disclosure. As seen in FIG. 4 and FIG. 5, the housing segments 104 have a hollow configuration and define a trapezoidal slot 104A, in accordance with one embodiment of the present disclosure. It is to be noted that the trapezoidal profile of the slot 104A is only exemplary, and the slot 104A may have any shape other than a trapezoidal shape. The circles 108A are the balls 108A of the actuator cable 108 that are accommodated in a socket configured within in the interior of one of the housing segments. The construction and operation of the ball and socket joint is described in the subsequent sections of the present disclosure.

Figure 7:
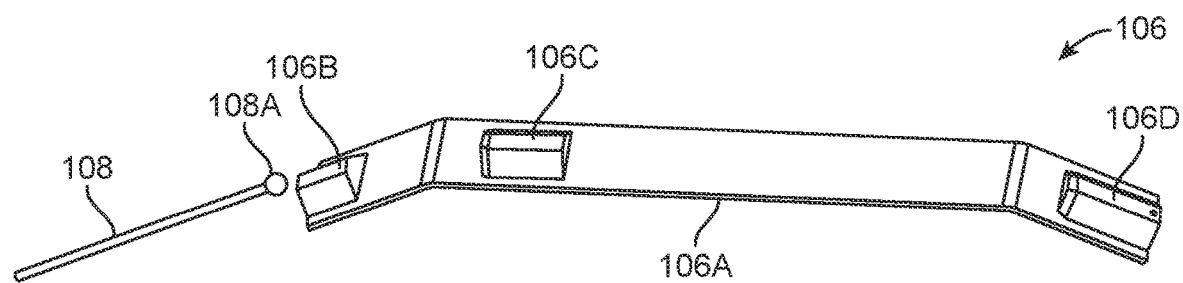
FIG. 7 illustrates a perspective view of a core element used in the occlusion clip, according to an embodiment of the present disclosure.

FIG. 7 illustrates a perspective view of the core element 106 used in the occlusion clip 100, in accordance with an embodiment of the present disclosure. The core element 106 comprises a base 106A and a plurality of tabs 106B, 106C, 106D. The plurality of tabs 106B, 106C, 106D have a shape complementary to a shape of an inner periphery of the housing segments 104. As mentioned before, the housing segments 104 have a hollow configuration, and according to one embodiment, the housing segments 104 define the slot 104A having a trapezoidal profile. As such, the plurality of tabs 106B, 106C, 106D may also have a trapezoidal shape that fits into the slot 104A in a way that they are moved in a linearly guided motion within the slot 104A when the actuator cable 108 is pulled backwards.

Referring back to FIG. 4A and FIG. 4B, the displaced position of the core element 106 are illustrated. More specifically, in the first stage of clip application, when the actuator cable 108 is pulled backwards, a small portion of the plurality of tabs 106B, 106C, 106D are displaced and positioned above the live hinges 102A, thereby effectively straightening out the live hinges 102A, while in the second stage of clip application, the plurality of tabs 106B, 106C, 106D are displaced and positioned above the live hinges 102A in a manner that one tab of the plurality of tabs 106B, 106C, 106D is positioned in between and extends substantially equal lengths into two adjacent housing segments 104, to make the housing segments 104 collinear and thus defining the closed state of the occlusion clip 100.

In one embodiment, the base strip 102 and the core element 106 are both made of resilient material, wherein both the components may be made of the same resilient material.

FIG. 8A through FIG. 8E illustrate different views of the core element 106, depicting the detailed features of a first tab 106B of the plurality of tabs 106B, 106C, 106D. It is to be noted that the first tab 106B has a construction that is different to that of the tabs 106C, 106D. This is because the first tab 106B is configured to interact with the actuator cable 108 for facilitating the movement linear guided movement of the core element 106 within the housing segments 104 for changing the state of the occlusion clip 100 from open to close. More specifically, the first tab 106B is configured to receive the actuator cable 108 securely until the actuator cable 108 is pulled out of the occlusion clip subsequent to the closing of the occlusion clip.

The first tab 106B comprises a rigid section 112 and a winged section 114. The rigid section 112 forms a block like structure from which the winged section 114 extends. The winged section 114 comprises a pair of wings 114' that extend outward hingedly and resiliently from laterally opposite ends of rigid section 112. More specifically, in an un-extended configuration of the pair of wings 114', the pair of wings 114' remain unhinged and in surface contact with each other, while the outward appearance of the first tab 106B resembles that of the tabs 106C, 106D. As such, the first tab 106B essentially has the same shape as the tabs 106C, 106D when the pair of wings 114' are in their un-extended state. While the appearance of the first tab 106B when the pair of wings 114' are hingedly extending outward is depicted in FIG. 7A and FIG. 7B.

Figure 8A:
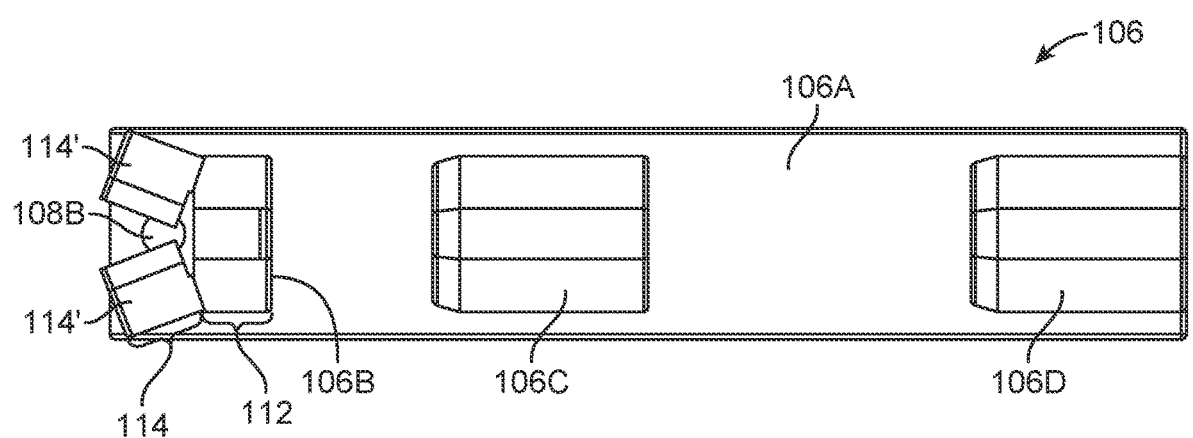
FIG. 8A through FIG. 8E illustrate different perspective views of the core element, according to an embodiment of the present disclosure.
Figure 8B:
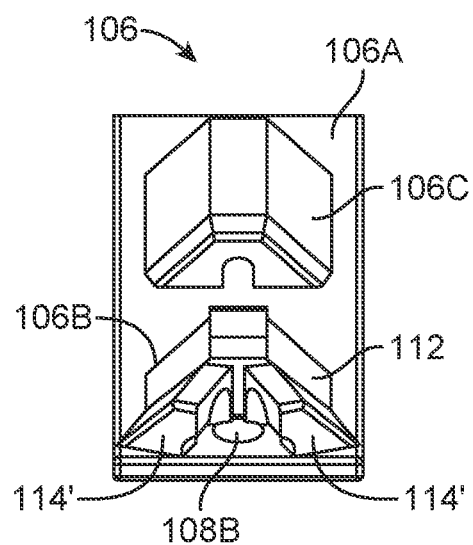
Figure 8C:
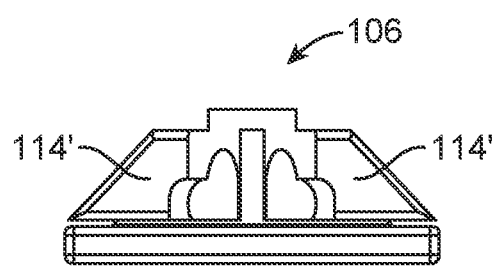

As seen in FIG. 8B and FIG. 8C, a receiving socket 108B is defined by depressions formed on a base 116 of first tab 106B below the pair of wings 114' and the inner surfaces of the pair of wings 114'. The receiving socket 108B, in accordance with one embodiment, is a spherical socket, wherein the spherical shape of the socket is formed when the pair of wings 114' are in their un-hinged closed state. In such a state, when the pair of wings 114' are in their closed configuration, a ball 108A of the actuator cable 108 is securely received and accommodated within the receiving socket 108B. This secure coupling between the pair of wings 114' and the actuator cable 108 the allows the core elements 106 to be pulled backwards without the cable 108 accidentally slipping out of the receiving socket 108B. The ball 108A of the actuator cable 108 may be removed from the receiving socket 108B when the pair of wings 114' are opened up, which gives extra clearance to the ball 108A of the actuator cable to come out of the receiving socket 108B.

Figure 8D:
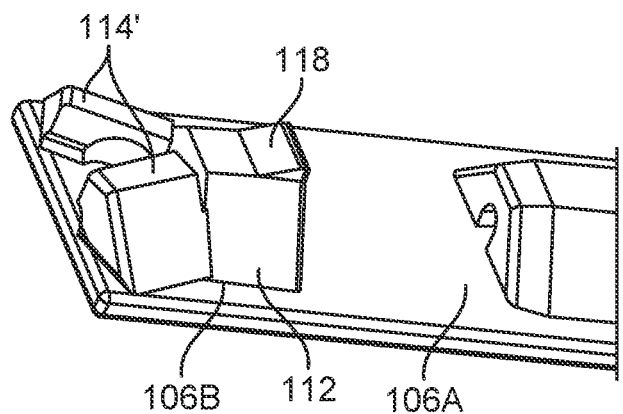
Figure 8E:
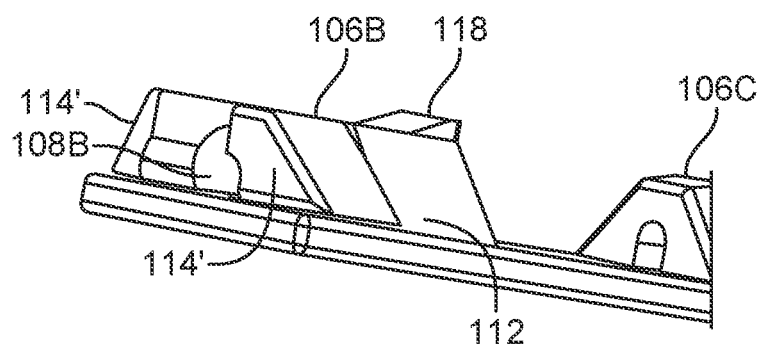

FIG. 8D and FIG. 8E illustrate perspective views depicting the first tab 106B, according to an embodiment of the present disclosure. As seen in FIG. 8D and FIG. 8E, the first tab 106B further comprises a locking protrusion 118. The locking protrusion 118 is a feature that controls and limits the travel of the core elements 106 within the housing segments 104, while at the same time influencing the opening the pair of wings 114' to release the actuator cable 108 therefrom.

Figure 9A:
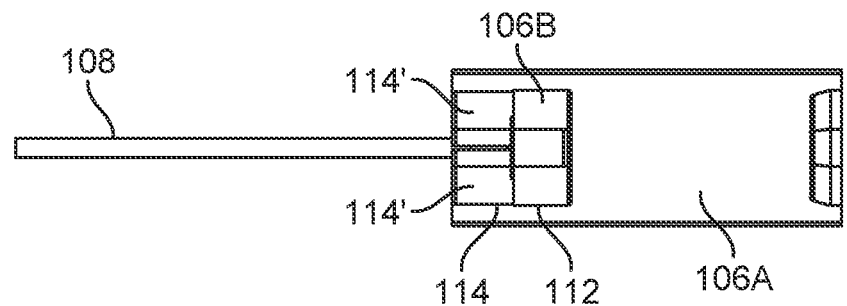
FIG. 9A through FIG. 9F illustrate different perspective views depicting the operation of actuator cables for facilitating actuation of the core element, according to an embodiment of the present disclosure.
Figure 9B:
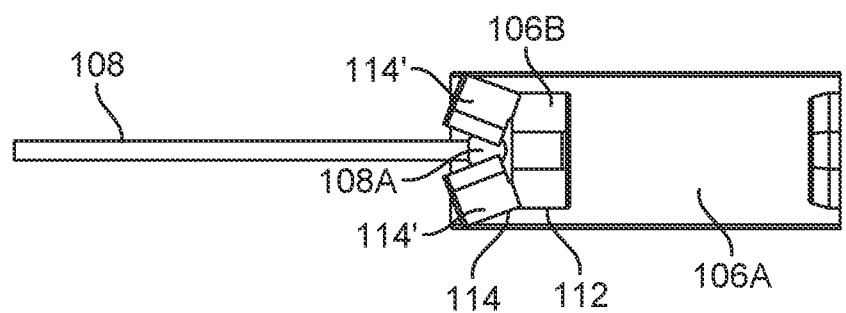

FIG. 9A and FIG. 9B depict the top views of the core element 106 when the ball of the actuator cable is accommodated within the first tab 106B, and when the ball of the actuator cable is about to be released from the first tab 106B, respectively. Referring to FIG. 9A, the pair of wings 114' are in their closed, unhinged state. In such a state, the ball of the actuator cable 108 is held within the receiving socket securely. Also, as seen in FIG. 9A, the first tab 106B has the trapezoidal configuration when the pair of wings 114' are in their closed un-hinged state that allows the first tab 106B to be accommodated within the trapezoidal slot 104A in the first housing segment.

Referring to FIG. 9B, the pair of wings 114' are shown to be opened, which gives extra clearance to the ball 108A of the actuator cable 108 for being released from receiving socket defined inside the first tab 106B.

Figure 9C:
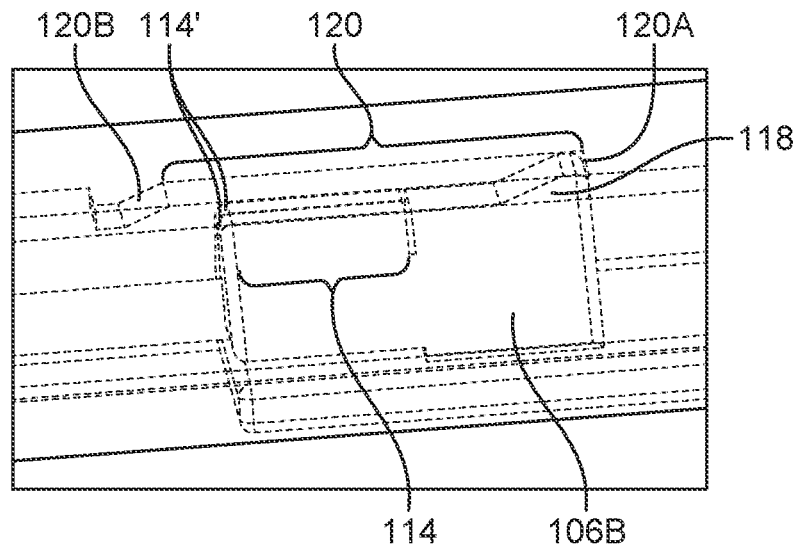

FIG. 9C through FIG. 9F illustrate closed up perspective views of the first tab 106B depicting the mechanism that controls the opening of the pair wings 114' and the release of the ball 108A of the actuator cable 108, according to an embodiment of the present disclosure. As seen in FIG. 9C, the first tab 106B includes a keyway 120 defined on an inner operative top surface of the first housing segment 104, wherein the keyway 120 is defined between a pair of spaced apart notches 120A, 120B. The length of the keyway 120 is the distance that the first tab 106B travels during the first stage of the closing process of the occlusion clip 100, in accordance with an embodiment of the present disclosure.

The locking protrusion 118 is provided for facilitating guided linear movement of the first tab 106B within the keyway 120. A first notch 120A is a back out preventer notch that allows abutment of the locking protrusion 118 formed on the first tab 106B for maintaining a position of the core element 106 within the plurality of housing segments 104 when the occlusion clip 100 is in its open state. A second notch 120B, spaced apart from the first notch 120A, has a shape complementary to that of the locking protrusion 118, wherein the second notch 120B is configured to allow abutment of the locking protrusion 118 thereon to prevent accidental opening of the occlusion clip 100 once the locking protrusion 118 is pulled beyond the second notch 120B. A third notch 120C is spaced apart from the second notch 120B and is the locking notch that the locking protrusion abuts when the clip 100 is locked in its final position by the surgeon after the triggering is performed by the surgeon in the second stage of occlusion clip closure, in accordance with an embodiment of the present disclosure.

As seen in FIG. 9C, the pair of wings 114' of the first tab 106B are closed. When the pair of wings 114' are closed, the first tab 106B is movable within the first housing segment 104, and the distance that the first tab 106B may travel within the housing segment is defined by the length of the keyway 120. As seen in FIG. 9C, when the actuator cable is pulled backwards, the locking protrusion 118 is pulled against the second notch 120B until it moves beyond the second notch 120B.

Figure 9D:
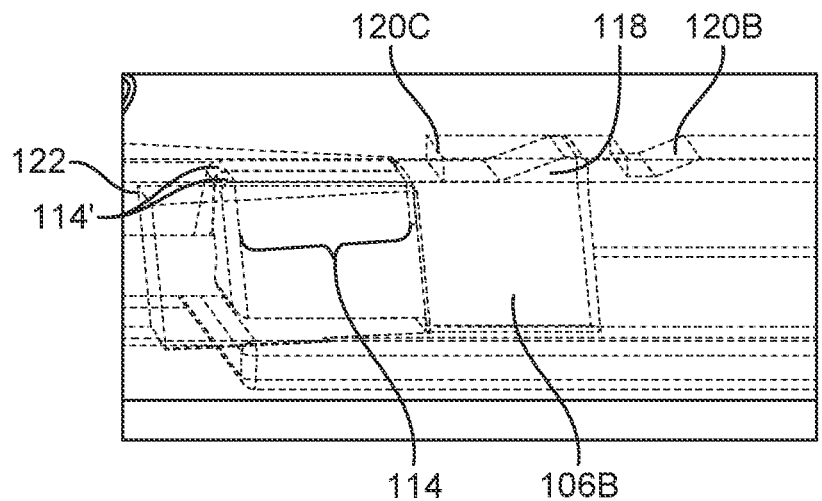
Figure 9E:
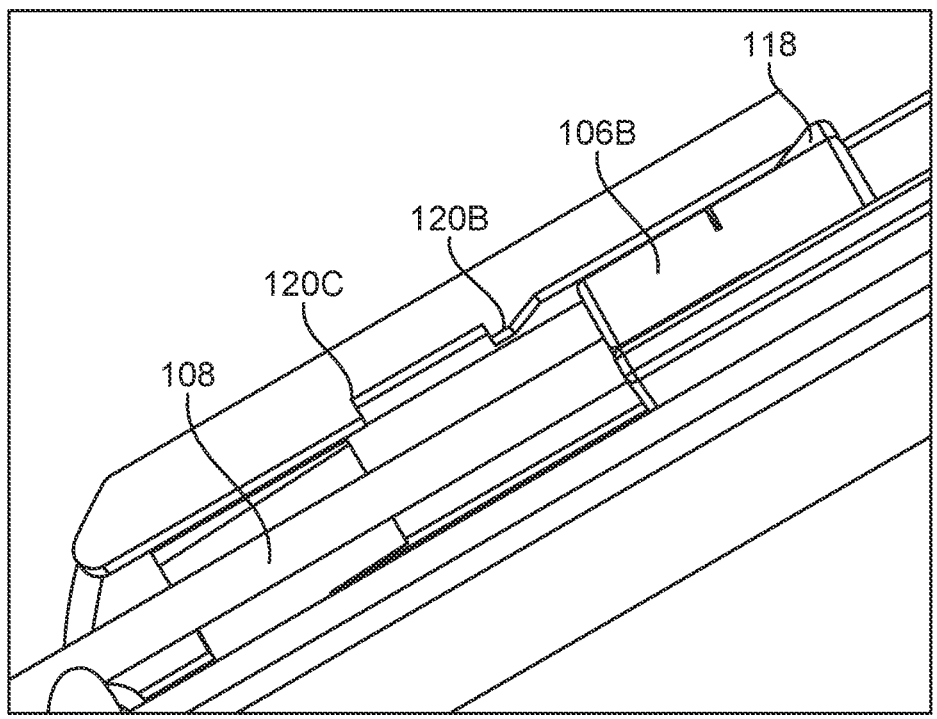

Referring to FIG. 9D, as the first tab 106B is pulled beyond the second notch 120B, the winged section 114 of the first tab 106B starts entering a locking cavity 122. As seen in FIG. 9D, the length of the distance between the notches 120B and 120C is substantially equal to the length of the locking cavity 122. In accordance with one aspect of the occlusion clip 100, the distance between the notches 120B and 120C or the length of the locking cavity 122 is the travel distance that the tab 106B travels subsequent to the triggering of the occlusion clip in the second stage of the occlusion clip closure. The locking cavity 122 is configured between the second notch 120B and an operative end of the first housing segment 104 for accommodating therein the spread opened pair of wings 114' after the first tab 106B is pulled beyond the second notch 120B. More specifically, the after the winged section 114 of the first tab 106B starts entering the locking cavity 122, the walls of the slot 104A keeping the pair of wings 114' in their closed state can do so no more as the surface contact broken when the pair of wings 114' enter the locking cavity 122, and the resilient nature of the pair of wings 114' causes the pair of wings 114' to extend outwardly in a hinged manner from the lateral ends of the rigid section 112. The locking cavity 122 accommodates the pair of wings 114' in their opened state and prevents the movement of the first tab 106B back in the direction towards the second cavity 120B.

Referring to FIG. 9A through FIG. 9E, the core elements 106, in accordance with one embodiment, may have about 3 mm of movement between open and closed positions of the occlusion clip 100. During the first stage of occlusion clip closure, a surgeon may actuate the manipulator head to pull the actuator cables 108 to close the clip 100, but if determined to be wrong, then the manipulator head may be used by the surgeon to go back and re-open the clip 100. More specifically, when lined up with the targeted tissue area, the surgeon may pull a handle lever to retract the actuator cables 108. On retraction, the actuator cable 108 may stop at a detent that may be part of the trigger in the handle, wherein the stopping of the actuator cable 108 is also influenced by its abutment on the notch 120B. The second stage of the occlusion clip closure is performed if the surgeon is satisfied with the positioning of the occlusion clip. More specifically, the surgeon may pull the handle lever/trigger an additional 0.5 to 1 mm to displace the core element 106 for securing the clip 100 and moving the locking protrusion 118 into a corresponding locking notch 120C, as seen in FIG. 9D. The keyway 120 depicts the aforementioned 3 mm travel distance travelled by the tab 106B in the first stage of the clip closure, and the additional 0.5 to 1 mm trigger distance is the distance between the notches 120B and 120C that is travelled by the tab 106B in the second stage of clip closure, in accordance with one exemplary embodiment of the present disclosure.

In one embodiment, the clip 100 in the open position has the housing segments 104 spaced apart by 15 mm apart. In another embodiment, this space may be as large as 65 mm. In accordance with one embodiment of the present disclosure, the aforementioned 3 mm travel of the core element 106 within the keyway 120 facilitated by the actuator cables 108 causes the clip 100 to go from the 15 mm open to 0 mm closed. In another embodiment, each of the tabs 106C, 106D may be provided with locking protrusion 118 and the corresponding keyways 120. As the locking protrusion 118 travels the last distance between the notches 120B and 120C, the winged section 114 moves into a larger locking cavity 122 laterally so that the wings 114' spread apart by built in tension, thus opening enough so that the ball 108A is pulled back by actuator cable 108 and pops out of the cavity 108B between the two wings 114'.

Figure 9F:
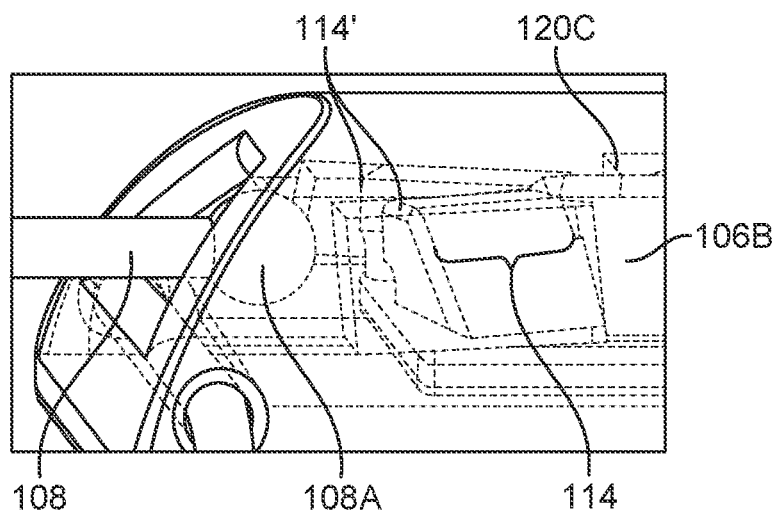

FIG. 9F illustrates a perspective view depicting the release of the ball 108A of the actuator cable 108 from the pair of wings 114', according to an embodiment of the present disclosure. As seen in FIG. 8E, as the pair of wings 114' open up, the receiving socket also opens up because of the spreading apart of the pair of wings 114', which in turn provides additional clearance to the ball 108A to be released from the receiving socket.

Figure 10:
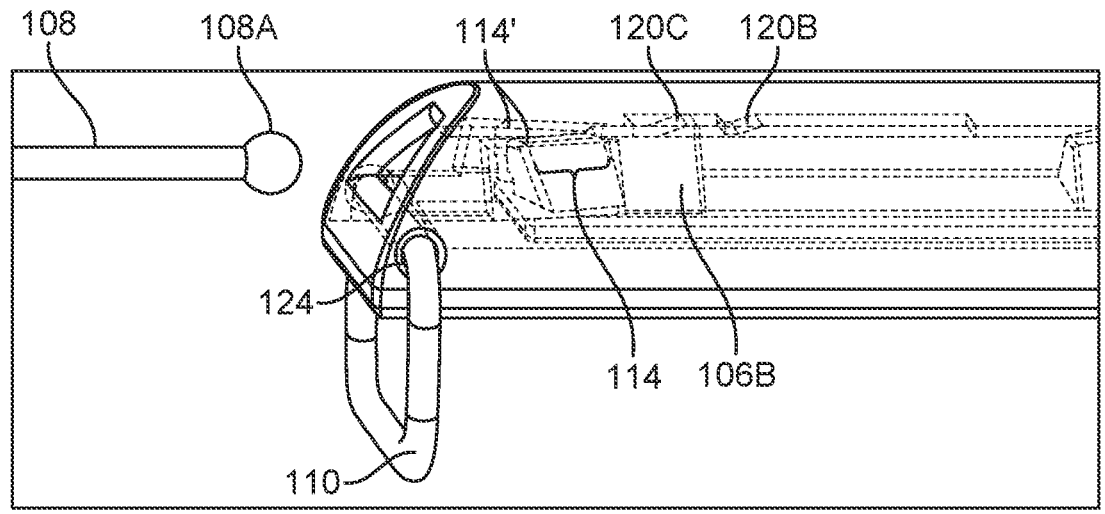
FIG. 10 illustrates another perspective view of the occlusion clip detailing the construction of a holder ring used in the occlusion clip, according to an embodiment of the present disclosure.

FIG. 10 illustrates a perspective view depicting the fitment of the holding ring 110 on the housing segment 104, according to an embodiment of the present disclosure. As seen in FIG. 1, FIG. 4A, and FIG. 10, the housing segments 104 that are provided on the operative ends the hexagonally looped base strip 102 are provided with a through-hole 124. The through-hole 124 allows the passage of the holding ring 110 therethrough. The holding ring 110 holds the free ends of the hexagonally looped base strip 102 together to ensure that the occlusion clip 100 remains looped in the form of a ring or a clip. As mentioned previously, the occlusion clip 100 may be changed into open state from its closed state by simply cutting off the holding ring 110. An advantageous aspect of the holding ring 110 is that it allows a surgeon to easily remove the occlusion clip 100 after applying it on a targeted tissue if the surgeon feels that the application was not done optimally and needs to be redone. In yet another aspect, the occlusion clip 100 may also be reopened by cutting open the operative end 100B of the occlusion clip 100.

Figure 11:
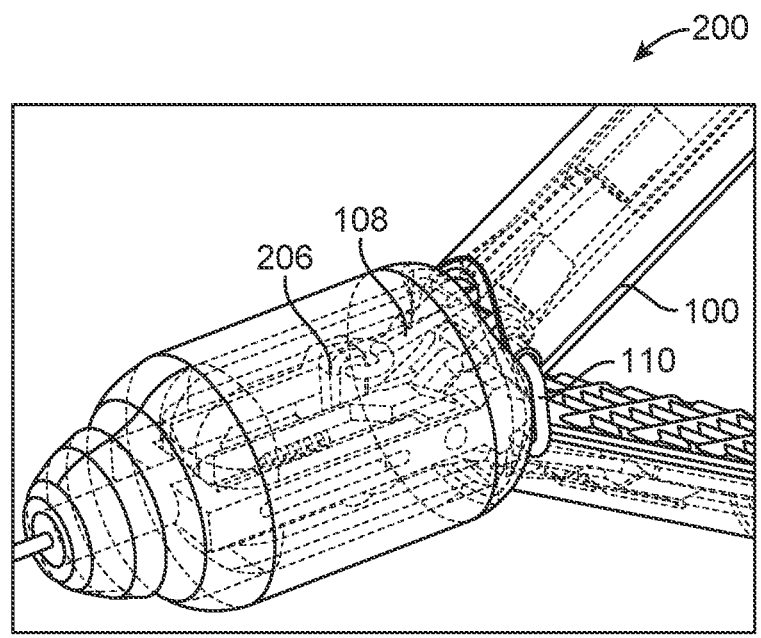
FIG. 11 and FIG. 12 illustrate perspective views of a manipulator head used for manipulating the occlusion clip, according to an embodiment of the present disclosure.
Figure 12:
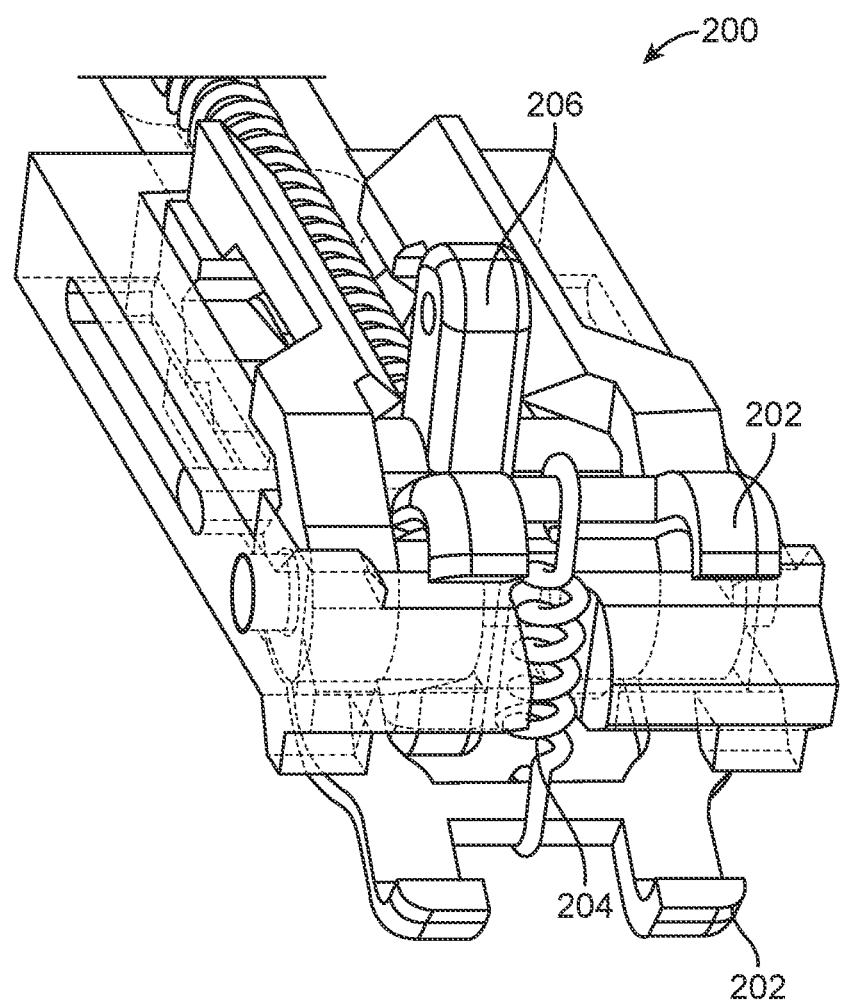

FIG. 11 and FIG. 12 illustrate views of an exemplary manipulator head 200 for securely holding the occlusion clip 100 thereon, in accordance with one embodiment of the present disclosure. A pair of jaws 202 on the manipulator head 200 is provided to hold on to the occlusion clip 100 thereon. A biasing element 204 keeps the jaws 202 gripping on the occlusion clip 100. It is to be noted that the biasing element 204 is an optional element, and other embodiments of the manipulator head 200 may be made sans the biasing element 204. The manipulator head 200 further comprises a holder 206 that is configured to hold on to the actuator cable 108. The holder 206 may be coupled to a robotic surgical system such as, for example, a DaVinci surgical system, that may facilitate the linear movement of the holder to affect the linear movement of the actuator cable 108, thereby changing the configuration of the occlusion clip 100 from an open state to a closed state.

Figure 13:
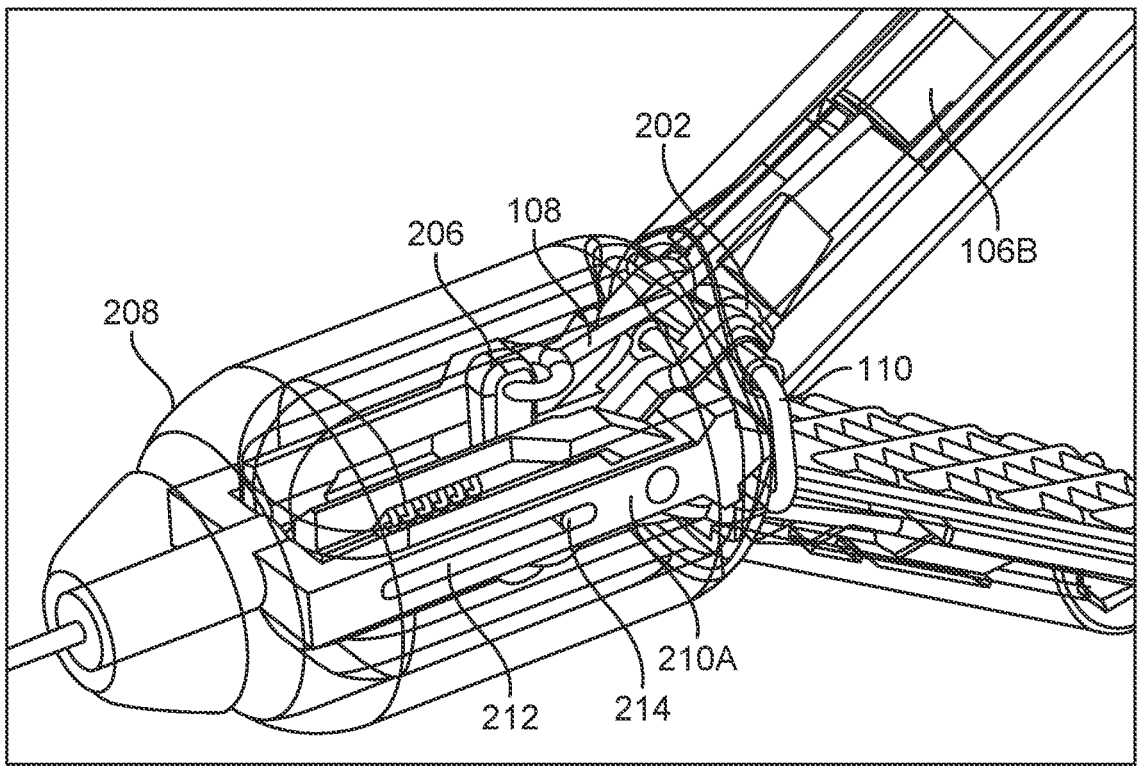
FIG. 13 through FIG. 15 illustrate perspective views of the occlusion clip assembled on the manipulator head, according to an embodiment of the present disclosure.
Figure 14:
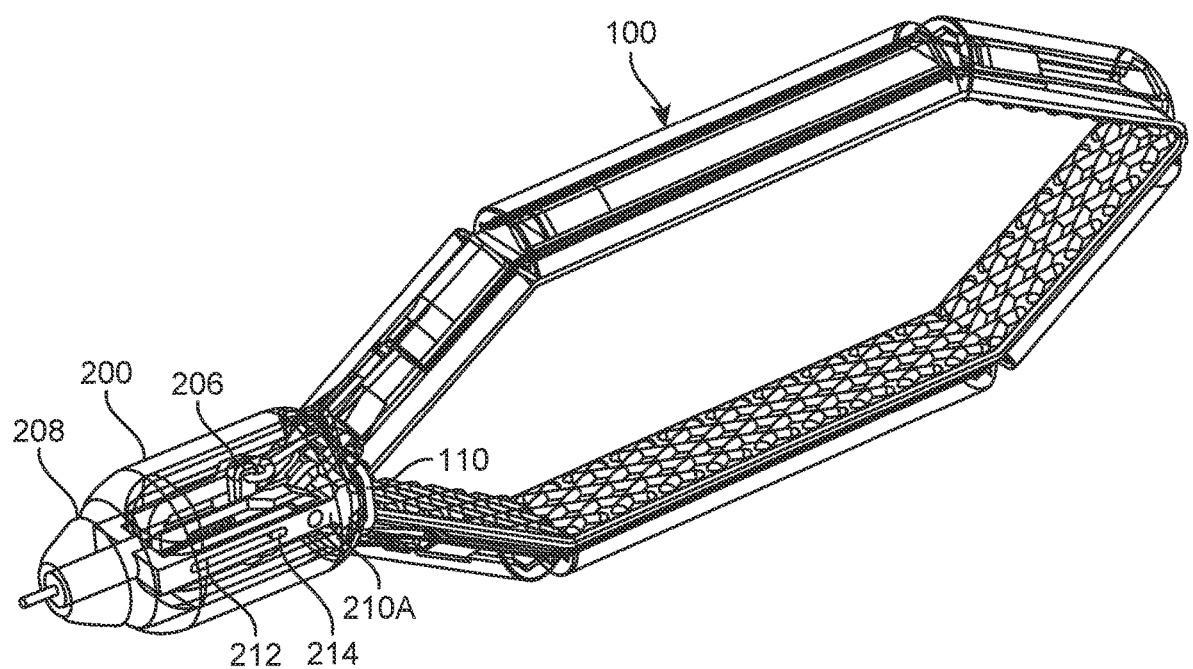
Figure 15:
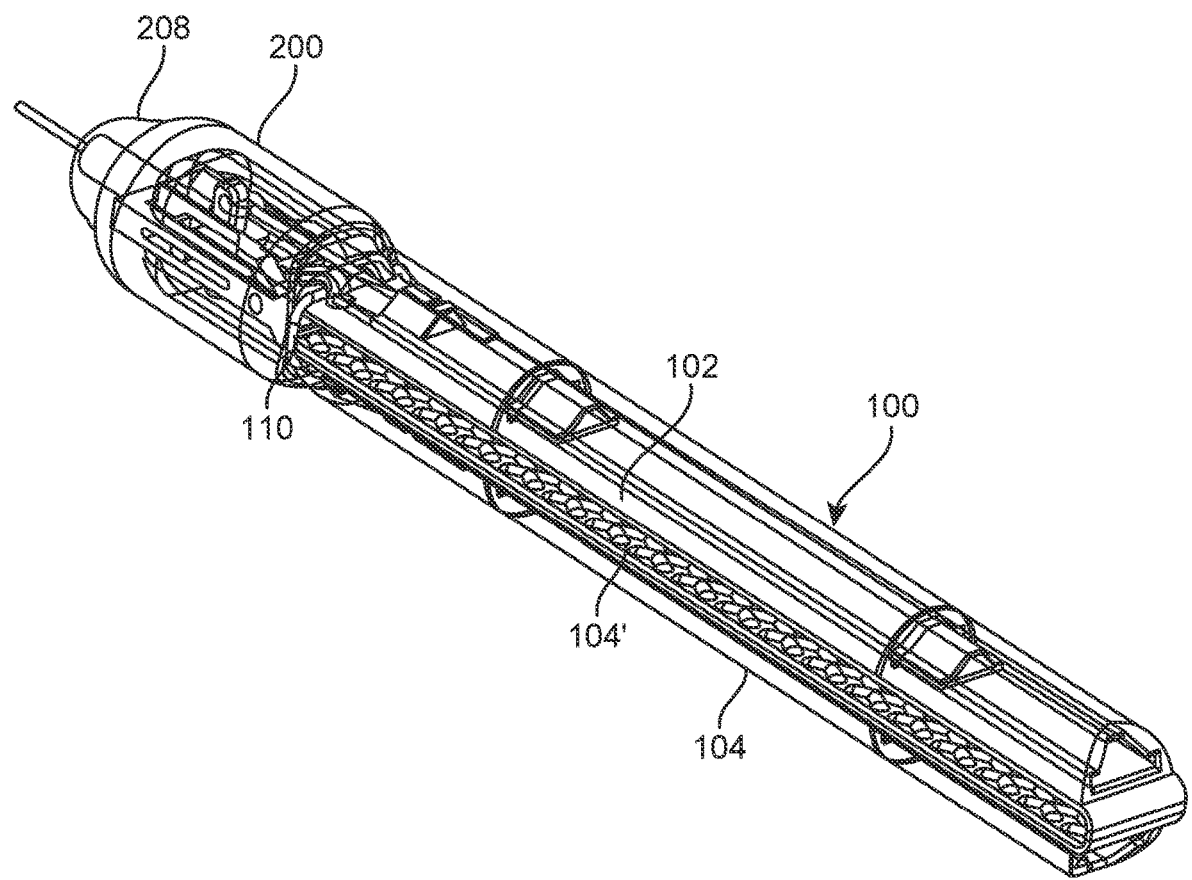

FIG. 13, FIG. 14, and FIG. 15 illustrate perspective views of the assembly of the occlusion clip 100 on the manipulator head 200, in accordance with an embodiment of the present disclosure. As seen in FIG. 13, the jaws 202 are configured to hold onto the holding ring 100. While the jaws 202 hold on to the holding ring 110, the actuator cables 108 are coupled the holder 206 and extend therefrom and terminate into the first tab 106B of the core elements 106. As the surgeon performs the first stage and second stages of the occlusion clip closure, the actuator cables 108 are retracted by effecting the retraction of the holder 206 that is controlled by the surgeon. FIG. 14 depicts the view of the occlusion clip 100 in its open state and coupled to the manipulator head 200, and FIG. 14 depicts the view of the occlusion clip 100 in its closed state and coupled to the manipulator head 200. It is to be noted that in FIG. 15, the occlusion clip 100 is closed after the surgeon has performed the first stage of clip closure and just before the second stage of the clip closure is performed.

Figure 16A:
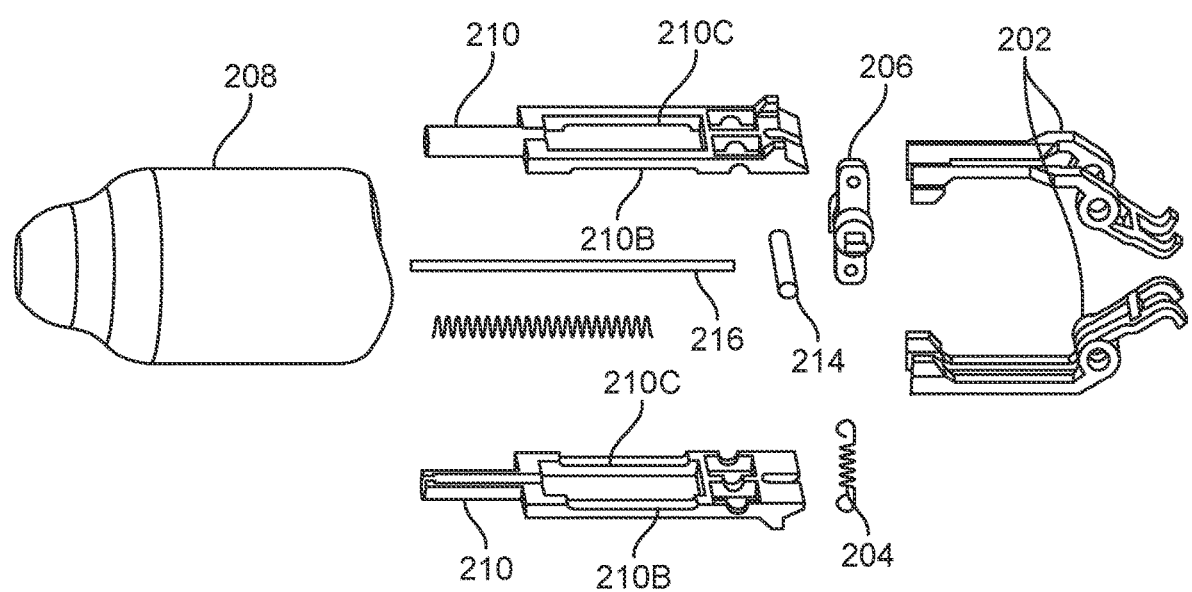
FIG. 16A and FIG. 16B illustrate views of the manipulator head for the occlusion clip, according to an embodiment of the present disclosure.
Figure 16B:
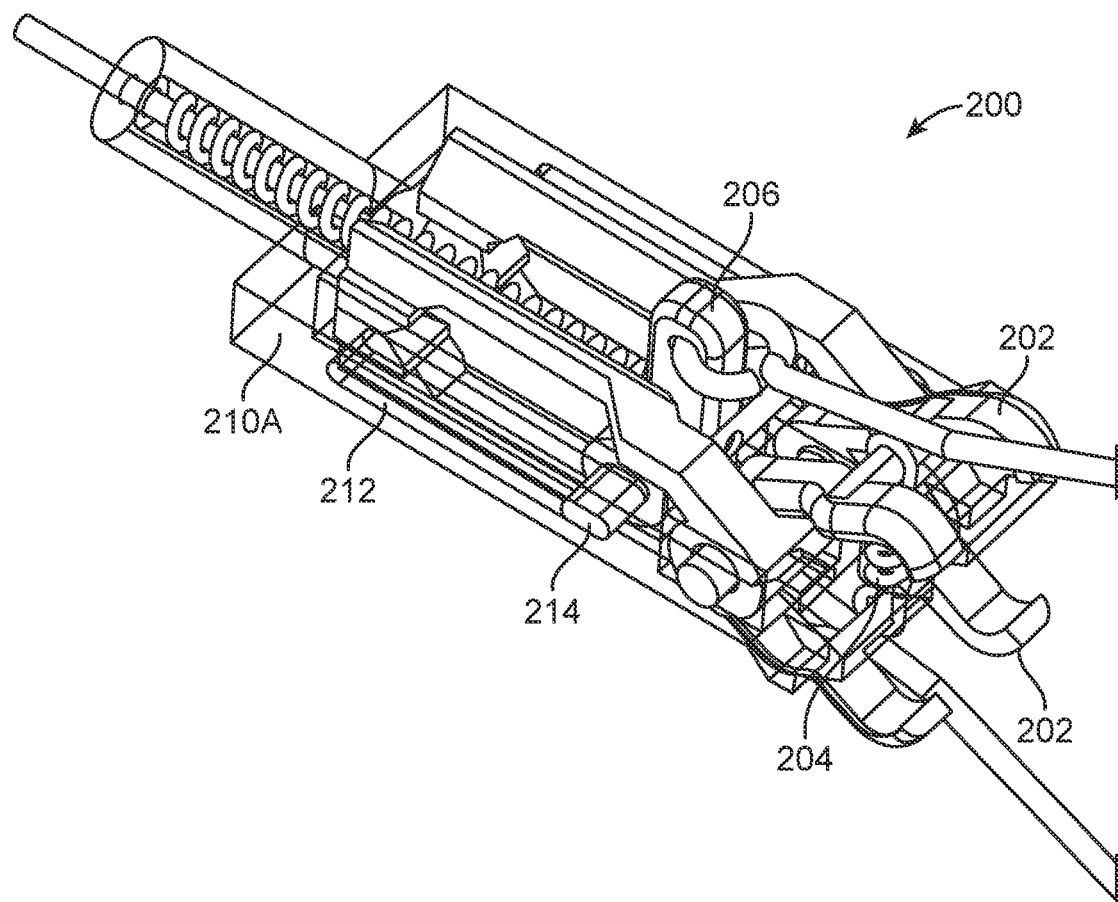

FIG. 16A and FIG. 16B illustrate views of the manipulator head 200, in accordance with an embodiment of the present disclosure. Referring to FIG. 13, FIG. 16A, and FIG. 16B, the manipulator head 200 comprises an outer cover 208. The outer cover 208 is configured to house in itself a pair of brackets 210, wherein the pair of brackets 210 are assembled together to define a single bracket holder 210A, as seen in FIG. 13. The bracket holder is configured to support the holder 206 thereon. A groove 210B is configured on each side of the brackets 210, which define a slot 212 when the pair of brackets 210 are assembled together. The holder 206 is configured to receive a lug 214, and the lug 214 coupled to a control cable 216 that is used by the surgeon for controlling the opening and closing of the clip. In an assembled configuration, the holder 206 is assembled within a rectangular space 210C defined by each of the brackets 210 and configured for linear movement therein, wherein the linear movement of the holder 206 is facilitated by the lug 214 that is coupled to the control cable 216 controlled by the surgeon. A biasing element 218 may be used for providing additional resilience against the linear movement of the holder 206 on retraction of the control cable 216 by the surgeon.

In accordance with an embodiment of the present disclosure, the manipulator head 200 is designed to be at the end of any tool that is used to apply the clip—be it a handle for "open" cases or an endoscopic clip applier or a sub-xiphoid applier. For use with the DaVinci system a few grasp points would be added to the housing of the manipulator head and a mechanism to allow grasping and pulling of the control cable.

The amount of force applied to the compressed atrial tissue is determined by the size of the hinge at 100B (FIG. 3B)— this will be set to 1.5 mm as it is what we have determined to be the commonest distance between the compressed walls of the base of the atrial appendage.

In one embodiment, the delivery device comprises a shaft having a proximal end and a distal end, a handle housing one or more controls connected to the proximal end of the shaft, and a manipulator head 200 connected to the distal end of the shaft. In one exemplary embodiment of such a suitable clip delivery device, the main components thereof comprise a control handle, an elongated shaft, and a manipulator head 200. In use, the control handle is oriented in a proximal direction (i.e., in the direction of the surgeon) to be manipulated by the surgeon. Further, the shaft forms an intermediate connection between the control handle and the clip-application manipulator head 200, such that the control handle is situated at the proximal end of the shaft and the clip-application manipulator head 200 is situated at the distal end of the shaft (the distal end being the farthest away from the surgeon).

In one embodiment, using the clip delivery device, the surgeon delivers the occlusion clip 100 (in its expanded state) into the thoracic cavity and to the location of the LAA. At this juncture, it is important to note that a variety of surgical methods for gaining access to the LAA may be employed and the instant exemplary exclusion procedure is not intended to be limited to any specific technique for accessing the LAA. For example, the LAA may be accessed by way of a conventional open-chest or open-heart procedure in which the surgeon makes a large incision in the middle of the chest and breastbone to have direct access to the heart. Alternatively, a left thoracotomy may be performed to create a small incision in the intercostal space between two adjacent ribs such that the clip delivery device is inserted through the chest wall. In a further alternative, a thoracoscopic procedure may be conducted to create several smaller incisions (referred to as "ports) in the chest wall to allow for the insertion of multiple instruments (e.g., a camera), including the clip delivery device. It should be appreciated that, in the case of accessing the LAA through lesser invasive surgical approaches (e.g., thoracotomy or thoracoscopy) in which small incisions are made, alternative exemplary embodiments of the clip delivery device may be configured to permit delivering the exclusion clip 100 to the site of the LAA while the clip 100 is in its unexpanded form in order to ease manipulation of the clip 100 through the small incision(s). In such embodiments, the exclusion clip 100 is placed into its expanded state after the clip has advanced into the thoracic cavity.

Figure 17A:
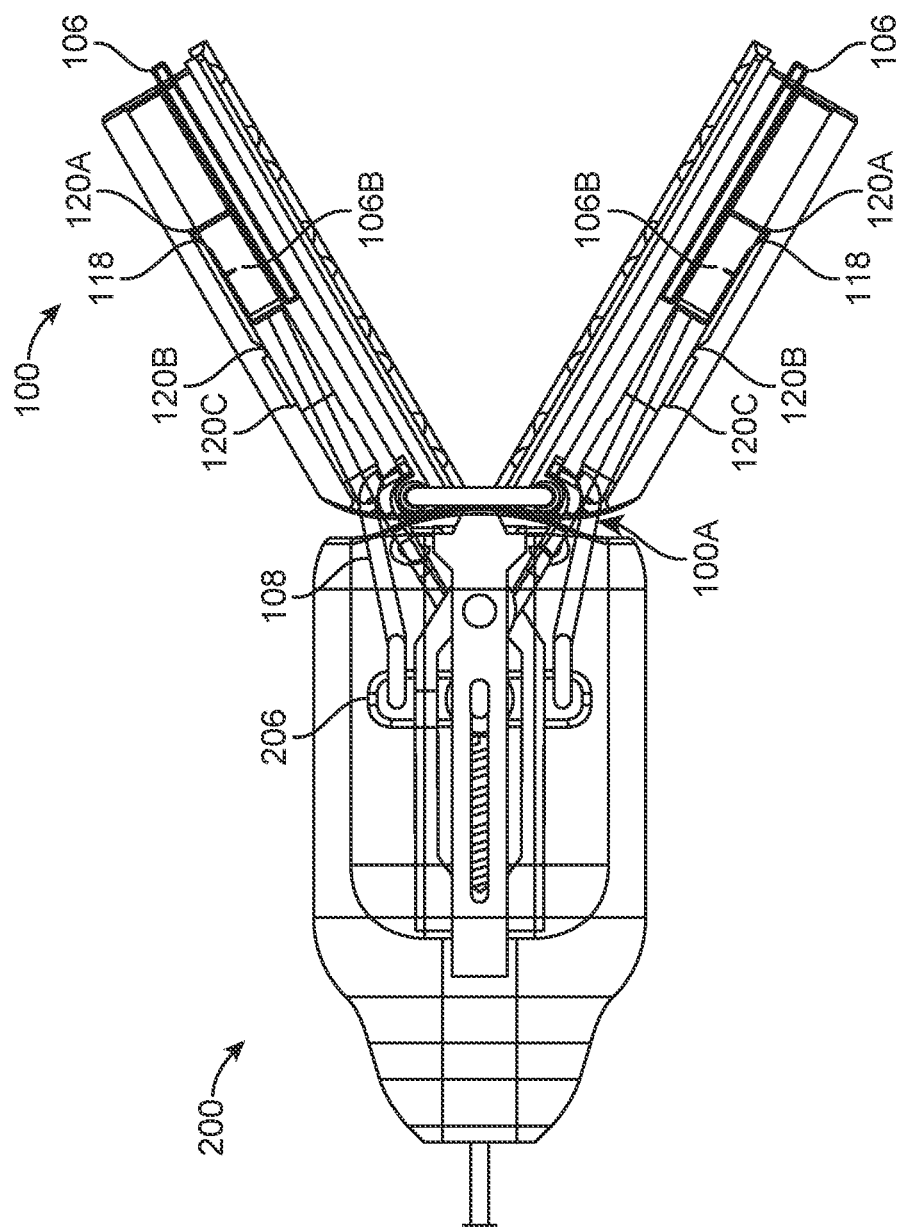
FIG. 17A though FIG. 17H illustrate different positions of the occlusion clip mounted on the manipulator head throughout a complete clip closure cycle, according to an embodiment of the present disclosure.

FIG. 17A though FIG. 17H illustrate different positions of the occlusion clip 100 mounted on the manipulator head 200 throughout a complete clip closure cycle, according to an embodiment of the present disclosure. Referring to FIG. 17A, the occlusion clip 100 is in an open configuration thereof. In this configuration, the locking protrusion 118 of the first tab 106B is in surface contact with the notch 120A, and the live hinges 102A of the occlusion clip 100 are bent thereby providing an open configuration to the clip 100 (as seen in FIG. 1 through FIG. 3A). Furthermore, in this configuration, the actuator cables 108 are in an un-retracted configuration. More specifically, the position of the actuator cable 108 is the start position, wherein the manipulator head 200 has not yet been manipulated to retract the actuator cable 108 for pulling the core elements 106 backwards towards the proximal end 100A of the clip 100.

Referring to FIG. 17B, the holder 206 is slightly retracted backwards, which causes the actuator cables 108 to slightly pull the core elements 106 backwards towards the proximal end 100A. The change in position of the core elements 106, the actuator cables 108, and the holder 206 is apparent on viewing the FIG. 17A and FIG. 17B in conjunction. Furthermore, referring to FIG. 17B, as the positions of the core elements 106, the actuator cables 108, and the holder 206 are slightly shifted backwards, the open configuration of the clip 100 can be seen as getting narrower as compared to that seen in FIG. 17A.

Figure 17C:
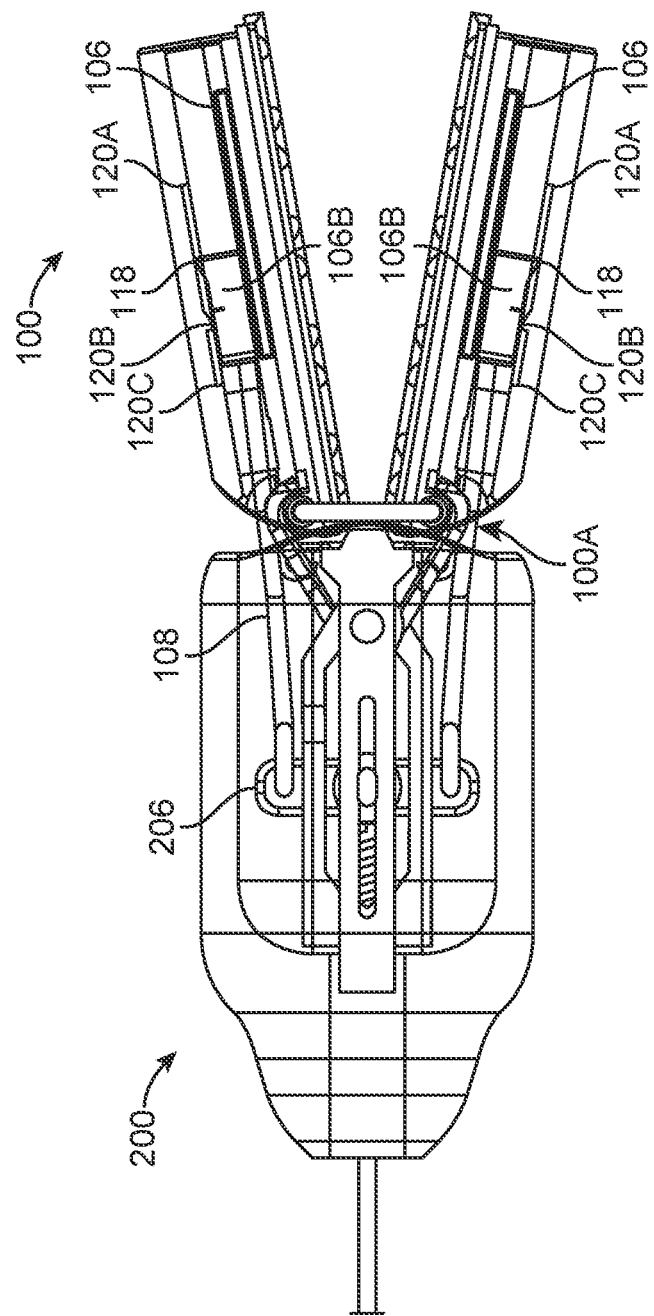

Referring to FIG. 17C, the holder 206 is again slightly retracted backwards, which causes the actuator cables 108 to slightly pull the core elements 106 backwards towards the proximal end 100A. The change in position of the core elements 106, the actuator cables 108, and the holder 206 is apparent on viewing the FIG. 17B and FIG. 17C in conjunction. Furthermore, referring to FIG. 17C, as the positions of the core elements 106, the actuator cables 108, and the holder 206 are slightly shifted backwards, the open configuration of the clip 100 can be seen as getting narrower as compared to that seen in FIG. 17B.

Figure 17D:
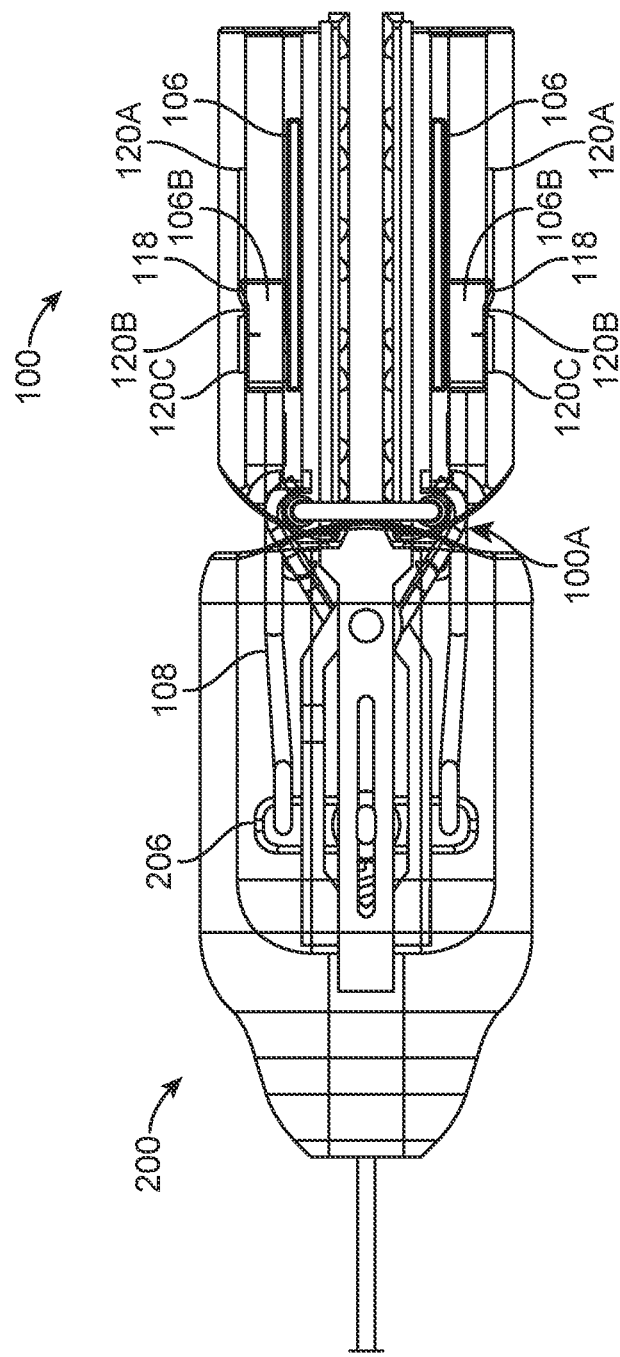

Referring to FIG. 17D, the holder 206 is again retracted slightly backwards. The configuration of the clip 100 depicted in FIG. 17D indicates the final position of the core elements 106, the actuator cables 108, and the holder 206 at the end of first stage of the clip closure cycle of the clip 100. As seen in FIG. 17D, the locking protrusions 118 of the first tabs 106B are in abutment with the notch 120B. In this position, the clip 100 is closed but not locked. If the surgeon feels that the placement of the clip 100 at the targeted tissue area is not optimal, the surgeon can move the holder, the actuator cables, and the core elements forward to reopen the clip 100, in which case the reopening of the clip 100 would follow the steps depicted in FIG. 17C, FIG. 17B, and FIG. 17A in the same order as mentioned, i.e., the clip 100 will open slightly at first as depicted in FIG. 17C, and then goes on opening all the way up to the position depicted in FIG. 17A.

Figure 17E:
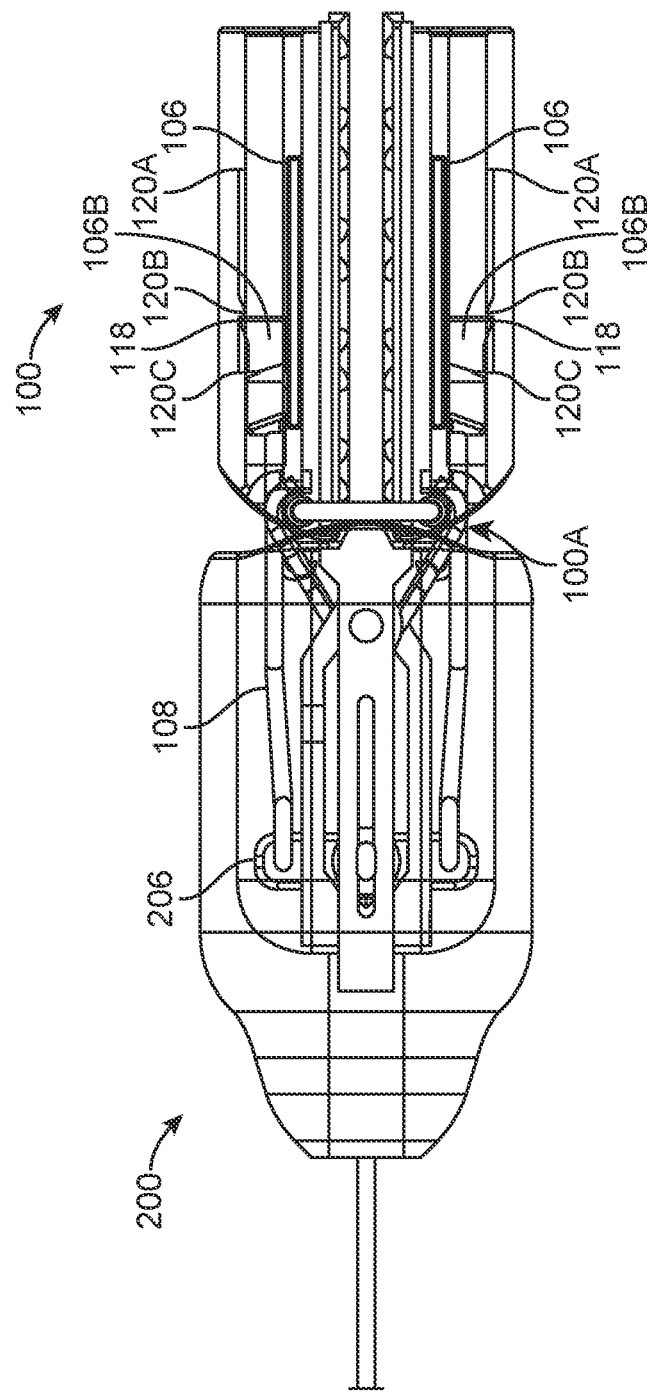

Referring to FIG. 17E, the holder 206 is again retracted slightly backwards relative to the position of the holder 206 in FIG. 17D. The position of the core elements 106 and the first tabs 106B indicates the beginning of the second stage of the clip closure cycle for the clip 100. More specifically, the locking protrusions 118 of the first tabs 106B are seen to have moved beyond the notch 120B. Such a movement of the locking protrusion 118 beyond the notch 120B may be triggered by the surgeon via a feature of the manipulator head once the surgeon feels that the placement of the clip 100 at the targeted tissue area is optimal.

Figure 17F:
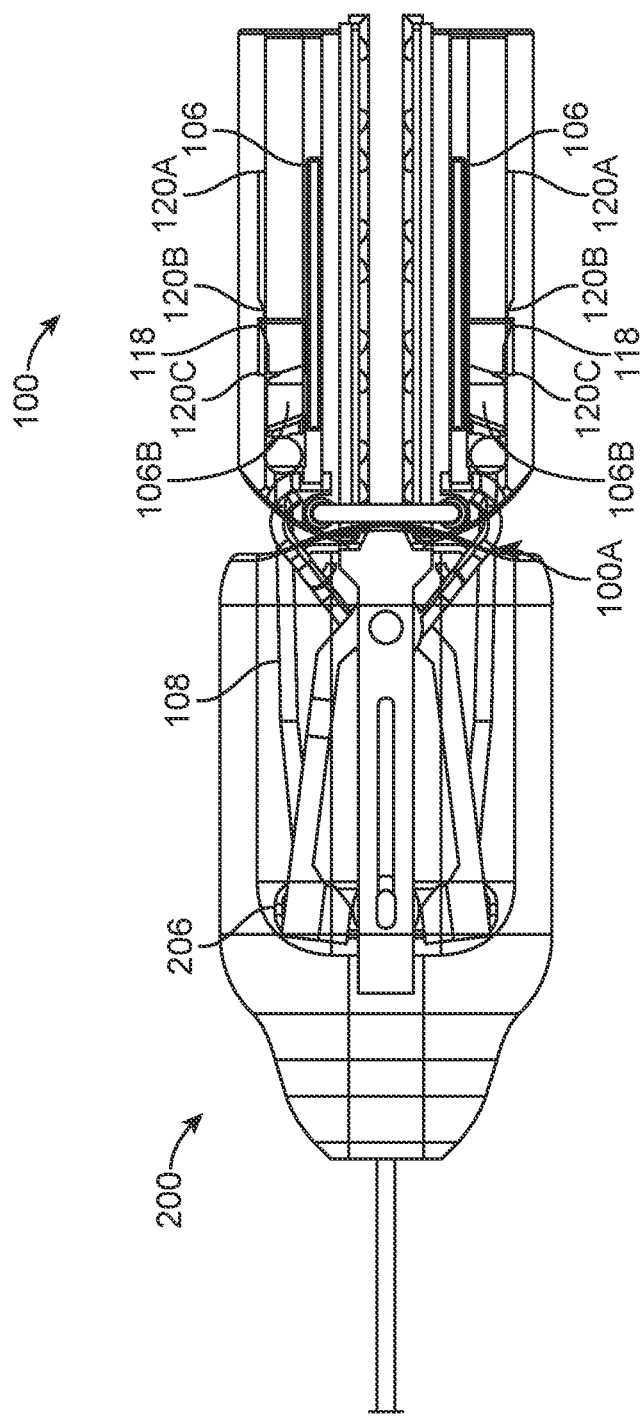
Figure 17G:
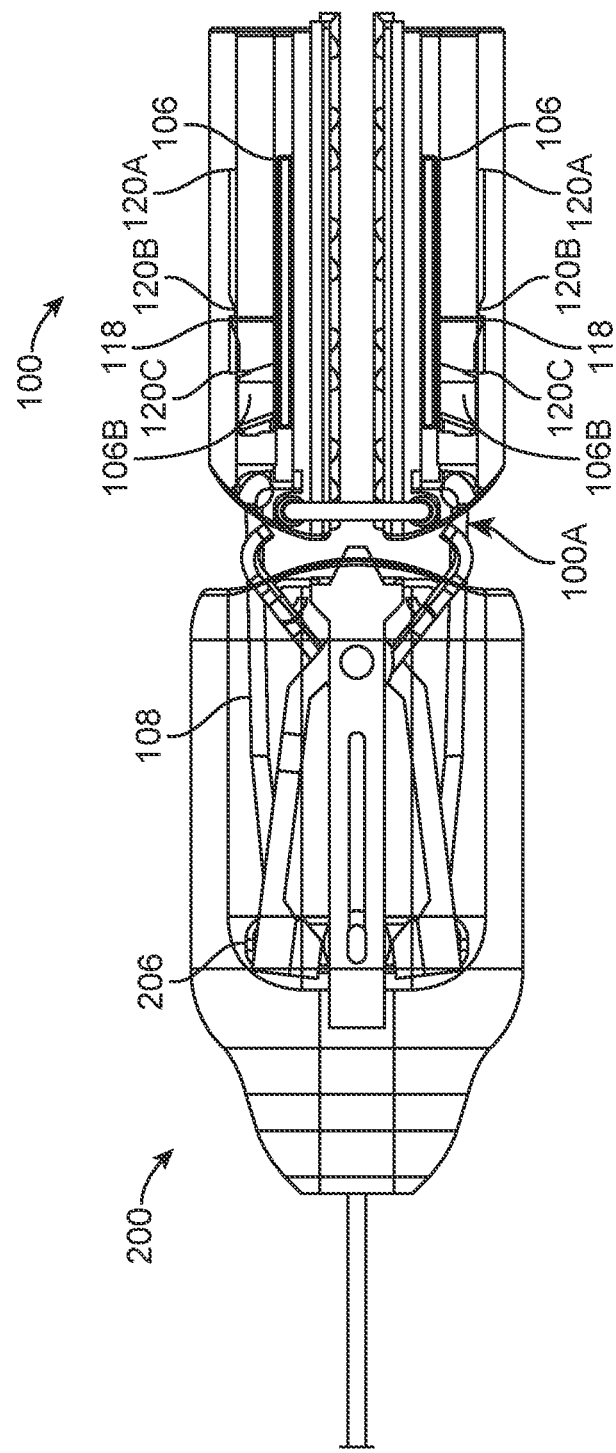

FIG. 17F through FIG. 17H illustrate the different positions of the actuator cables 108 being released from the first tab 106B after the surgeon has triggered the complete locked closure of the clip 100, in accordance with an embodiment of the present disclosure.

FIG. 18A through FIG. 18E illustrate different views of a clip opener 300, in accordance with an embodiment of the present disclosure. The clip opener 300 is a feature of the occlusion clip 100 that allows a surgeon to reopen the occlusion clip 100 if the surgeon feels that the fitment of the occlusion clip 100 at the targeted tissue was not executed optimally. More specifically, the surgeon need not cut open the holding ring to change the state of the occlusion clip 100 from closed state to its open state. The construction, features, and operation of the clip opener 300 is hereinafter described.

The clip opener 300 comprises the third tab 106D that is disposed within the housing segment 104 adjacent the distal end 100B of the occlusion clip 100. The third tab 106D is fitted inside the slot 104A defined in the interior of the housing segment 104. In one exemplary embodiment, a spring 304 may be optionally coupled to a rear end of the third tab 106D, and a block 306 is coupled to a free end of the spring 304. More specifically, the clip 100 is designed to contain inherent resilience and tension that in the rested position, the clip 100 retains its open ring like configuration; the spring 304, however, may be optionally provided to the clip opener 300 if in certain cases additional tension is needed to retain the clip 100 in its open configuration.

Figure 18A:
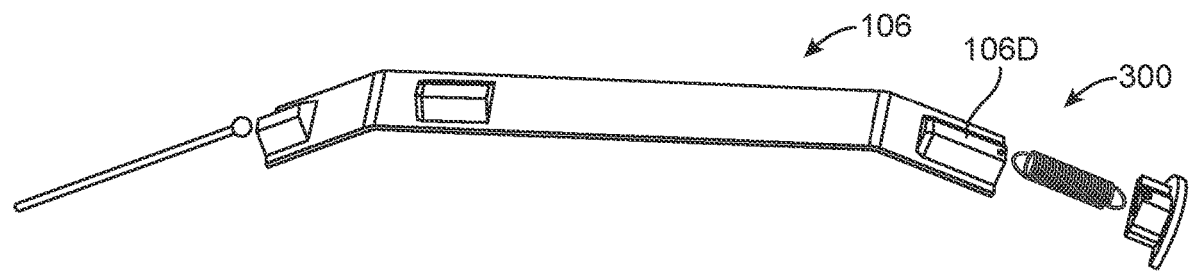
FIG. 18A through FIG. 18E illustrate different views of a clip opener, in accordance with an embodiment of the present disclosure.
Figure 18B:
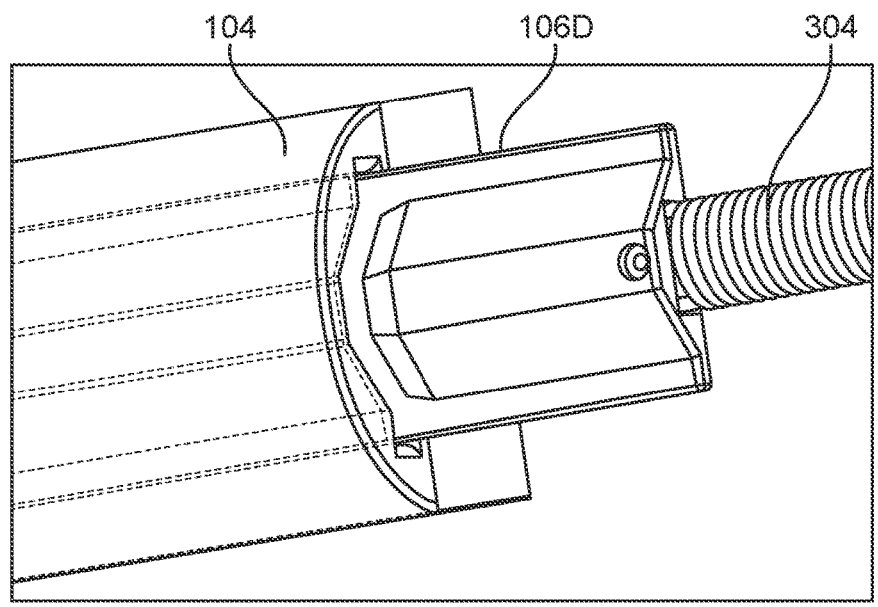
Figure 18C:
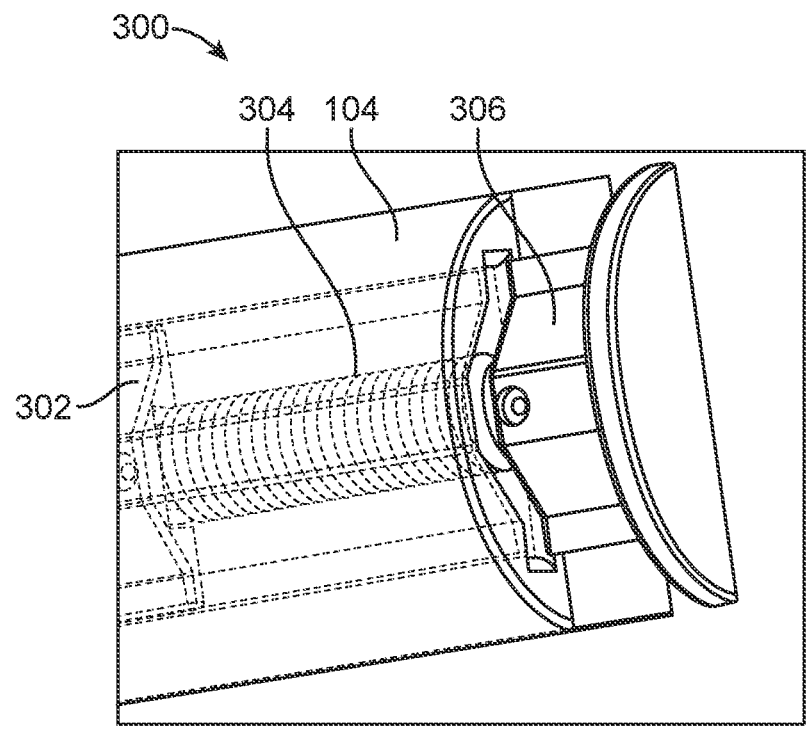
Figure 18D:
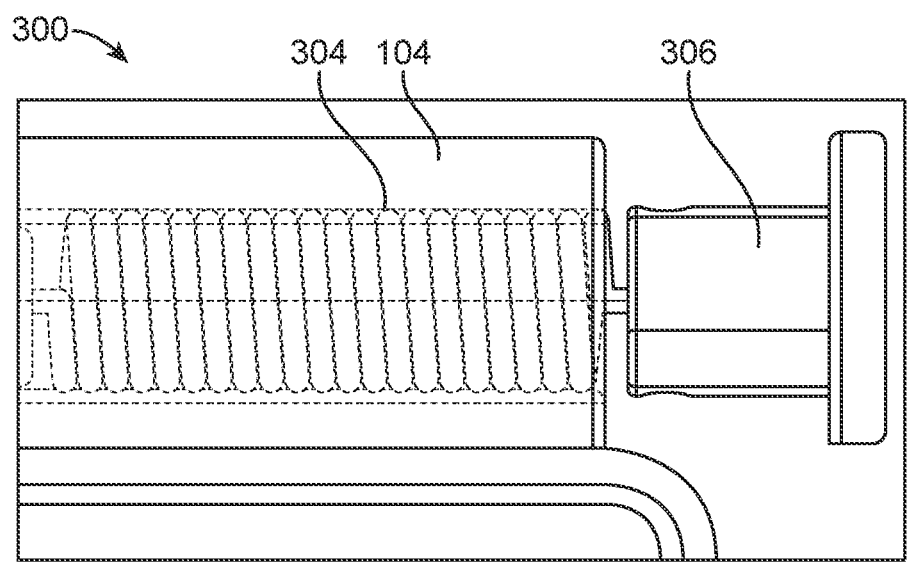
Figure 18E:
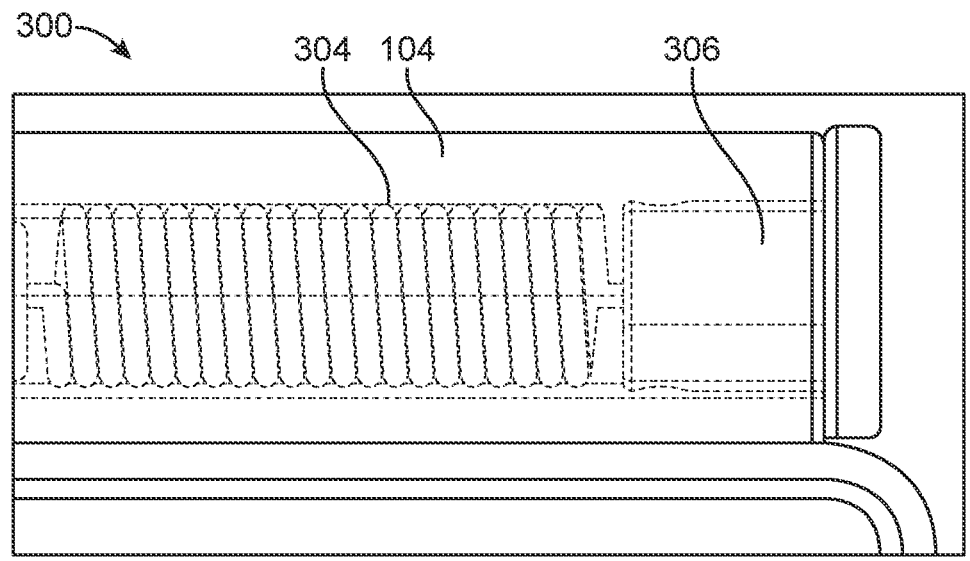

FIG. 18B illustrates a perspective view depicting the manner in which the spring 304 is coupled to the rear end of the third tab 106D. FIG. 18C illustrates a perspective view depicting the manner in which the free end of the spring 304 is coupled to the block 306, and the manner in which the block 306 is assembled on the housing segment 104. More specifically, in the rest position, the block 306 is not slid inside the housing segment 104, and the block 306 protrudes out from the housing segment 104, as illustrated in FIG. 18D. A pressure may be applied on to the block 306 by the practitioner using a feature of the manipulator head or the handling system on which the manipulator head is used. The application of the pressure causes the block 306 to slide completely inside the housing segment 104, as illustrated in FIG. 18E, which provides the clip 100 with a push required to change the state of the clip 100 from closed state to an open state.

One exemplary method of applying a pressure or pulling force on the block 306 is to pull the core elements 106 backwards, which causes the block 306 slide inside the slot 104A, where the spring 304 assists in the displacement of the block 306. It is to be noted that the in the first stage of clip closure, it is possible to maneuver the actuator cables to facilitate linear reciprocation of the core elements within pre-set limits. In this scenario, the spring 304 provides additional tension required to pull the block 306 into the housing segment 104. As the block 306 snaps into the housing segment 104, the clip 100 resumes its rested open state. More specifically, as the block 306 snaps into the housing segment 104, it causes the live hinges of the base strip to bend and change the state of the occlusion clip from the closed state to the open state.

In accordance with another exemplary embodiment, a string (not shown in figures) may be provided and looped around the entire body of the occlusion clip 100 while being in the surface contact with the end 100B of the clip. In order to reopen the closed shut occlusion clip 100, the surgeon pulls the string to apply pressure on the end 100B of the clip 100. It is to be noted that the string may be used when clip 100 is not resilient enough or does not have the inherent tension, and the spring 304 is also not used. In such an embodiment, the clip 100 and the string may be made of a resorbable material.

Figure 19:
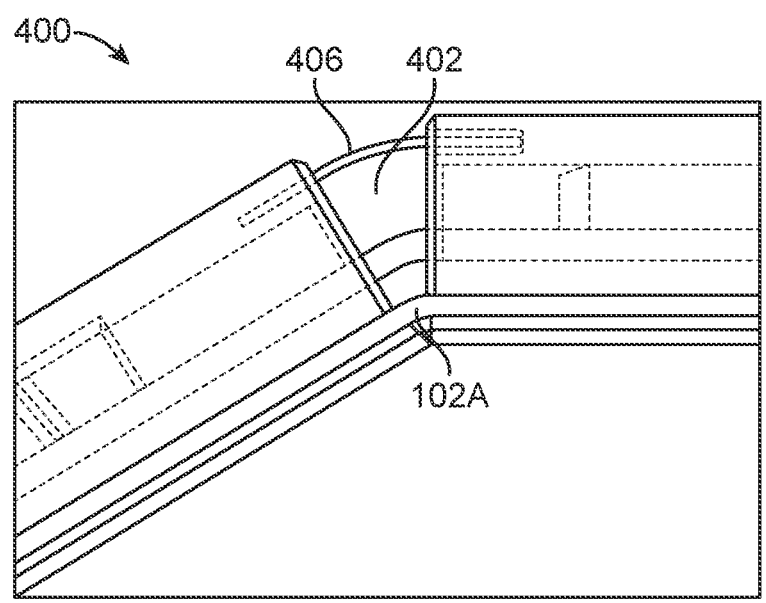
FIG. 19 illustrates a closed side view of the occlusion clip depicting an anti-pinch feature of the occlusion clip, in accordance with an embodiment of the present disclosure.

FIG. 19 illustrates a closed side view of the occlusion clip depicting an anti-pinch feature 400 of the occlusion clip, in accordance with an embodiment of the present disclosure. As mentioned previously, occlusion clip 100, in accordance with one embodiment of the present disclosure, may have a hexagonal shape in its open state. However, as seen in FIG. 19, a pinch zone 402 is formed between two adjacent housing segments 104 just above the live hinge 102A. As the occlusion clip 100 is closed shut, there is a possibility that some tissue other than the targeted tissue may get trapped inside the pinch zone 402 as the occlusion clip 100 is closed shut. This is not desired. To this end, the present disclosure envisages the anti-pinch feature 400. The anti-pinch feature comprises a resilient barrier 404 provided above the pinch zone 402 to cover pinch zone 402 for preventing entry of the surrounding tissue inside the pinch zone 402. The resilient barrier 404 is operatively coupled to and positioned between two adjacent housing segments 104. When the occlusion clip 100 is closed shut, the resilient barrier 404 may be housed within slots 406 configured in the housing segments 104.

In one embodiment, the resilient barrier 404 may be two spaced apart bands that are coupled to the housing segments. In another embodiment, the resilient barrier 404 may be a sheet of resilient material that forms a roof like structure over the pinch zone 402, thereby preventing the entry of the surrounding tissue therein.

Figure 20:
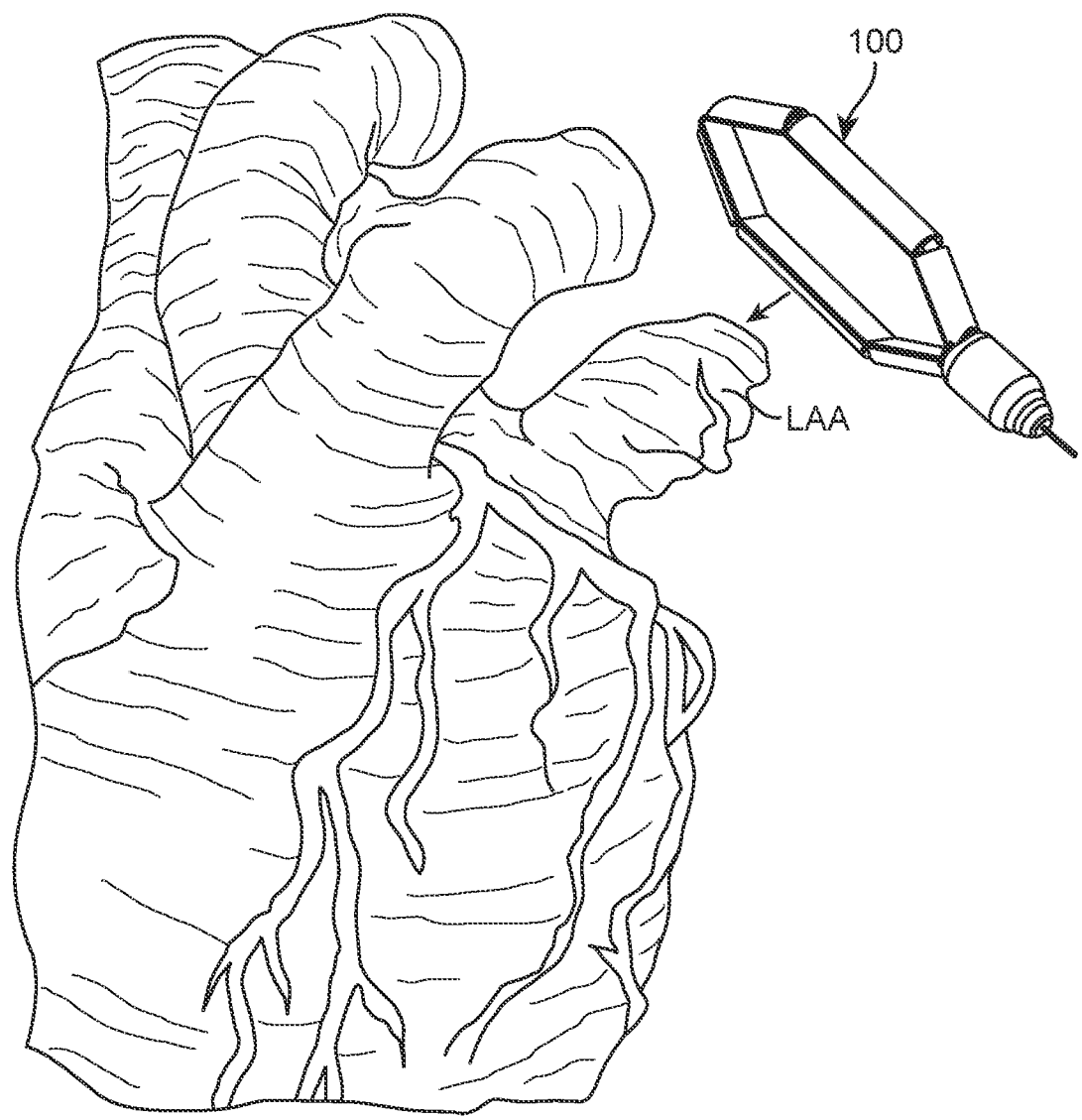
FIG. 20 and FIG. 21 illustrate schematic views of the occlusion clip being applied to a left atrial appendage of the human heart, according to an embodiment of the present disclosure.
Figure 21:
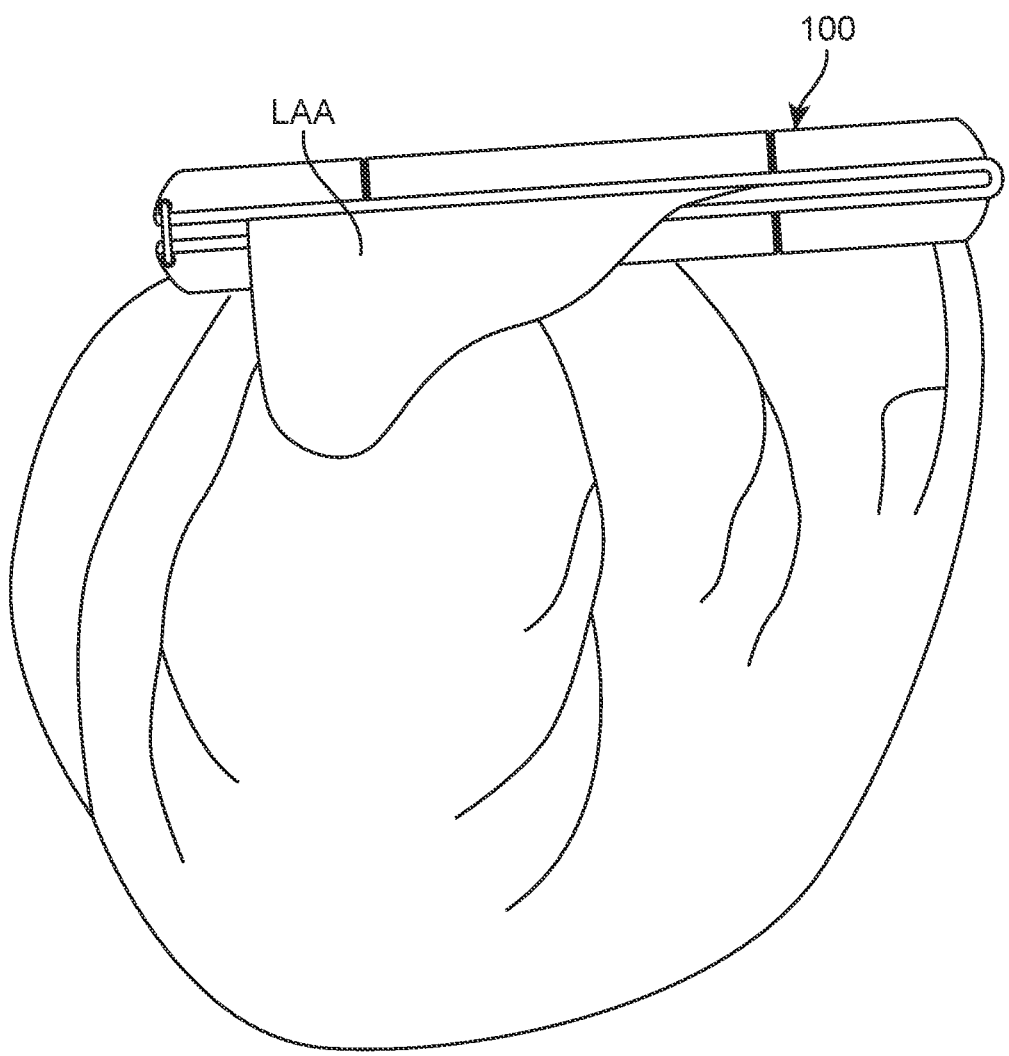

FIG. 20 and FIG. 21 illustrate schematic views of the clip 100 being applied on a left atrial appendage LAA of a human heart, according to an embodiment of the present disclosure. Referring to FIG. 19, the clip 100 is mounted on the manipulator head 200 and the manipulator head 200 may be coupled to any surgical system or applier such as sub-xiphoid applier or an endoscopic applier. FIG. 21 illustrates the schematic view after the clip 100 is applied onto the left atrial appendage LAA.

Several of the embodiments described herein use mechanical motion to provide pressure or force to the tissue being treated. In addition to or instead of the mechanical force, any of the clips described herein may be formed of a resilient material, such as NITINOL or other superelastic or elastic material. Using a resilient material allows the clip to be pre-stressed, such that when the clip is closed, the residual forces in the clip material continue to provide active pressure on the tissue within the clip.

Another version of the clip would be preloaded or stressed. In this version, the clip is made of a resilient material and pre-formed in the closed position. For installation, the clip would be deformed to allow the user to place the clip over the tissue. When the clip is released, the clip would return to the closed position, conforming to the shape of the tissue and clamping, compressing or otherwise manipulating the tissue.

Herein, the LAA-contacting pad is described as being of various materials. In an alternative exemplary embodiment, the clip 100 can be completely enclosed with a woven sleeve that provides a non-slip surface and promotes tissue ingrowth, e.g., it can be made from braided Dacron®. Another alternative to a pad of fabric is a smooth or textured surface or a surface covered with an elastomeric (e.g., polyurethane or polydimethylsiloxane) smooth or textured pad, possibly fitted with self-motivator materials as described above or with features that otherwise enhance traction against the LAA.

The clips described above may be configured to enclose a distal portion of the tissue to be clamped. Further, the clips may be configured to apply sufficient compression to the two tissue structures located in the clip, such that contact between the tissue structures is maintained under normal anatomical circulatory pressures of a patient. The arms or plates may be designed to apply approximately evenly distributed force or pressure along the length of the clip or alternately may be designed to apply greater force or pressure at one or more selected locations along the length of the clip. If desired, the clip may be closed or tightened in stages, such that after an initial amount of closure, the clip and/or tissue may be further adjusted prior to applying the full force to be eventually used. The device may also incorporate a mechanical or electrical/mechanical sensor that determines with adequate compression has been applied.

The motion of the clip and the associated motions of the applier, may be driven by any suitable mechanism, including but not limited to mechanical advantage, $CO_2$ pressure, vacuum pump, AC and/or DC power. The tissue may also be manipulated using an additional arm mounted on the clip, the clip applier or on a separate device. The additional arm may take the form of a probe, a grasping element, a vacuum source, a cutter and/or ablation device. These additional devices may be used before, during or after clip application.

Any of the above-indicated clips may also include any one or more options devices. Tissue engaging projections or fasteners, such as spikes, staples, rivets, sutures, and clips, may extending from one or both of the arms or plates. The tissue fasteners may be formed of a resilient, elastic or superelastic material. The tissue fasteners may be integrally formed with the arms of the clip, mounted within the clip or mounted within a cartridge that may be loaded into the clip. An alternate form of tissue attachment may be provided by a layer of adhesive on one or both arms of the clip. An energy source, such as RF or laser, may be used to treat or ablate the tissue near or within the clip. Clot detections devices may be mounted on the clip or on the applier and one or more needles may be used to withdrawal detected clots.

A vacuum source may be connected to the needles to use suction to withdraw the clots. Additionally, the device may incorporate a sensor, such as UV, IR or electrical, that has the ability to determine electrical block and/or transmurality.

The tissue clamping device may be formed of a resilient material, thereby continuing to apply direct pressure to the tissue enclosed within the clip after the clip has been closed.

The tissue clamping device is used to alter the natural proximity of two tissue structures by displacing a first and second tissue structure with a tissue clamping device; bringing the first tissue structure into contact with the second tissue structure; and applying sufficient pressure with the tissue clamping device to the first and second tissue structures such that intimate contact between the first and second tissue structures is maintained under normal anatomical circulatory pressures of the cardiovascular system. The tissue clamping device may be used temporarily during surgery or it may be permanently applied. The clip and clip applier may be used directly or through another instrument, such as a visualization device, cannula or other surgical instrument. If used for treating the left atrial appendage, the tissue clamping device may be applied via a direct intercostal approach between the 4th thru 6th intercostals space.

When one or more of the clips is used to treat the left atrial appendage LAA, the procedure may be done during full open-heart surgery or during minimally invasive surgery. A possible direct approach to the left atrial appendage during a minimally invasive procedure would be an intercostal approach between the ribs, in particular an approach between the 4th thru 6th intercostals space. Further, the clip and clip applier may be introduced via a visualization device.

In some procedures, one or more additional devices may be introduced into patient as a part of the clip applier or in addition to the applier. These include devices such as a visualization device, positioning or ablation device, such as one or more of the devices described in U.S. patent application Ser. No. 10/272,446, which has been previously incorporated by reference. The present invention and the auxiliary devices may be introduced into the patient via a primary incision placed in any suitable location. For example, in one embodiment the primary incision comprises a sub-zyphoid incision, but in other embodiments a subcostal incision, an intercostal incision or any other suitable incision may be used. To facilitate introduction of visualization device, one or more retractors may be used to increase the size of an incision. One or more additional incisions on patient may include, for example, an arterial/venous access incision for providing access for a perfusion cannula to a cardiopulmonary bypass machine or for any other device, an incision for a separately introduced left atrial appendage clamp or clip, and/or a femoral incision for providing access to a femoral artery for entry of a mapping catheter or any other device. Any suitable combination of incisions and devices is contemplated within the scope of the invention.

Several versions of device applicators are disclosed herein, these may be configured to partially or completely release once in place over the tissue to be treated. If this is the case an additional tool may be used to move the device between the open and the clamped or closed position. Releasing or decoupling the device from the applicator avoids translation or magnified translation of motion caused by dissimilar motions between the moving operator and moving tissue structure, minimizing trauma to the tissue structure to be altered.

The actuation of the embodiments may be set to move two arms simultaneously to move two tissue structures together simultaneously or the arms may be moved separately such that the majority of the motion is provided by one arm and the associated tissue moving towards the second tissue and corresponding arm. The pressure or force applied to the tissue may be used bring two tissues closer together, to seal an opening or to cut through and remove a portion of the tissue.

In each of these cases described for treating the left atrial appendage, the force applied to the tissue should be sufficient pressure or force to create and maintain contact between the top and bottom tissue structures of the left atrial appendage and to prevent the passage of fluid therethrough during pressures up to and/or slightly above normal anatomical circulatory pressure. Once sealed, the appendage may be left in place or may be partially or completely removed by ablation or dissection.

Each of the clips described herein are designed to enclose the distal end of the at least one tissue structure prior to application of forces between device and tissue. Further, the clips may be designed to apply relatively even distribution of force along the longitudinal axis of the tissue that is in contact with the clip. In some cases, it may be desirable to have one or more higher pressure area(s). In these cases, the clip would be configured such that a larger force would be exerted at a chosen location(s) along the length of the clip.

Figure 22:
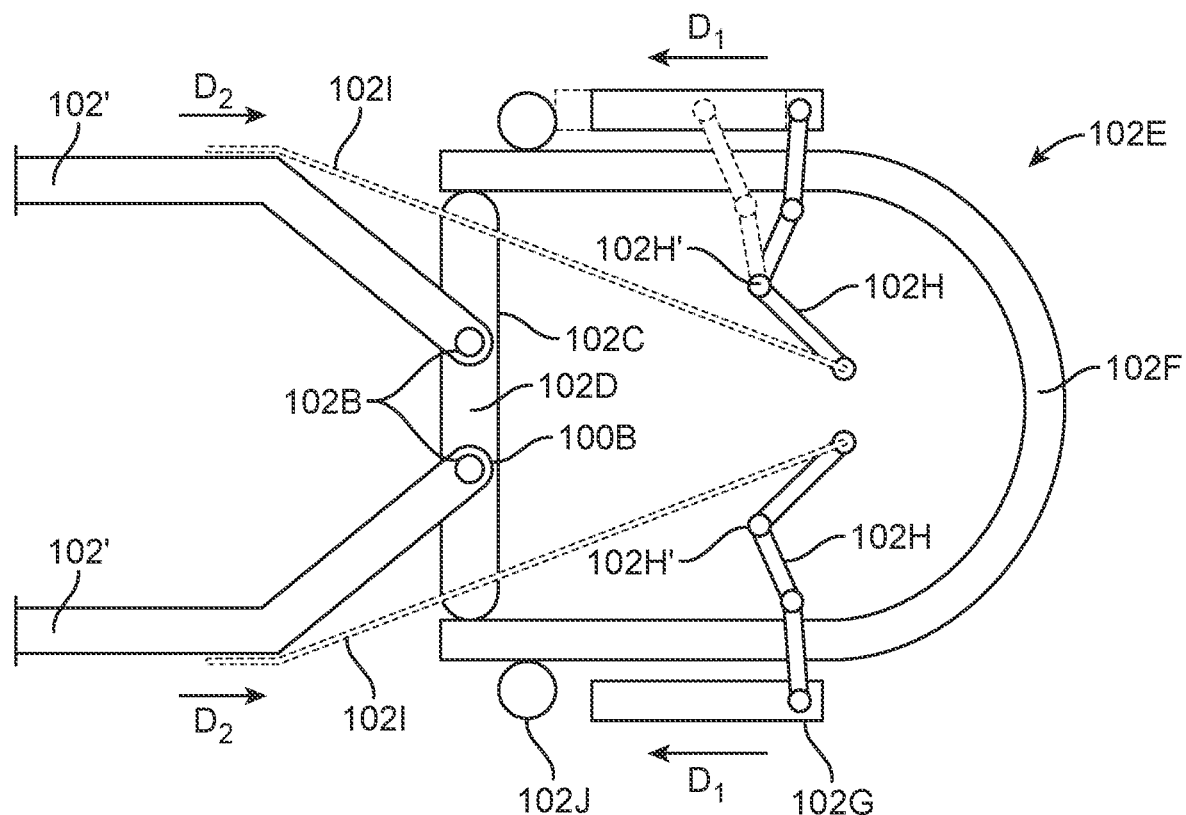
FIG. 22 through FIG. 24 illustrate schematic views of a distal end assembly for the occlusion clip, according to an embodiment of the present disclosure.
Figure 23:
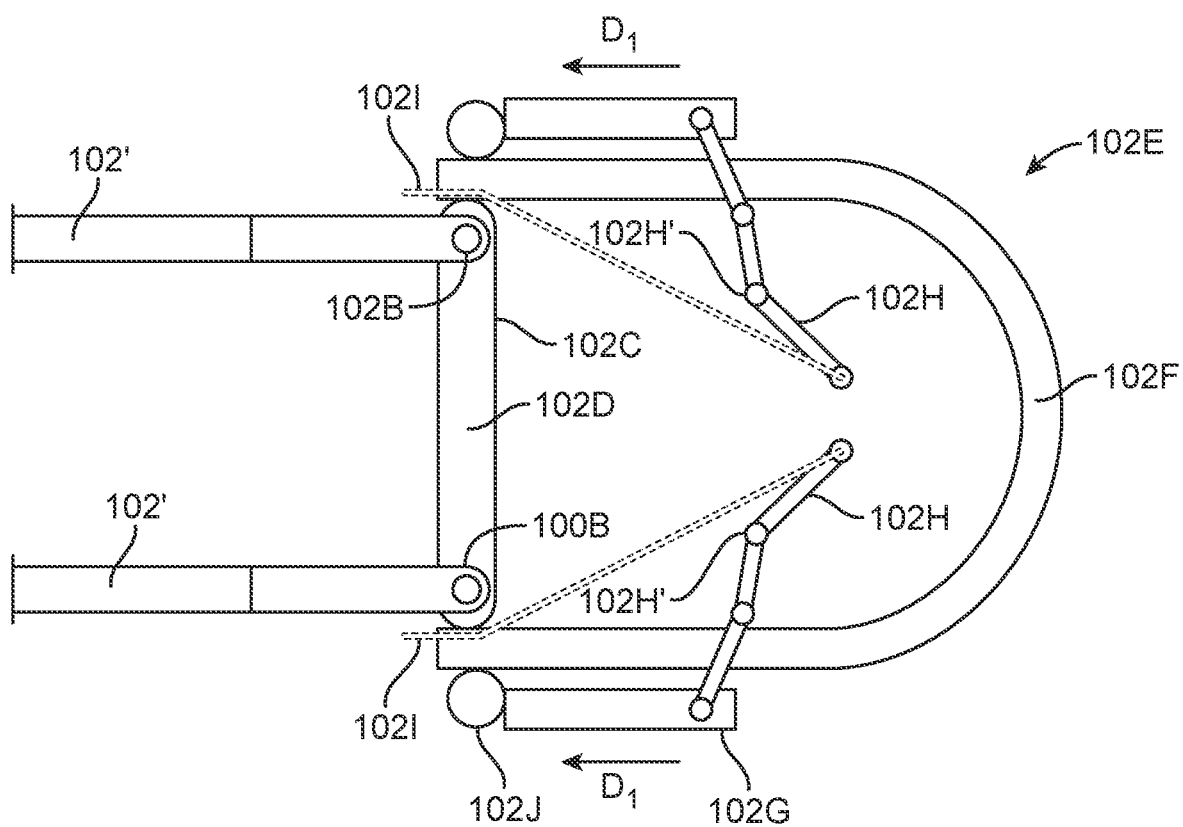
Figure 24:
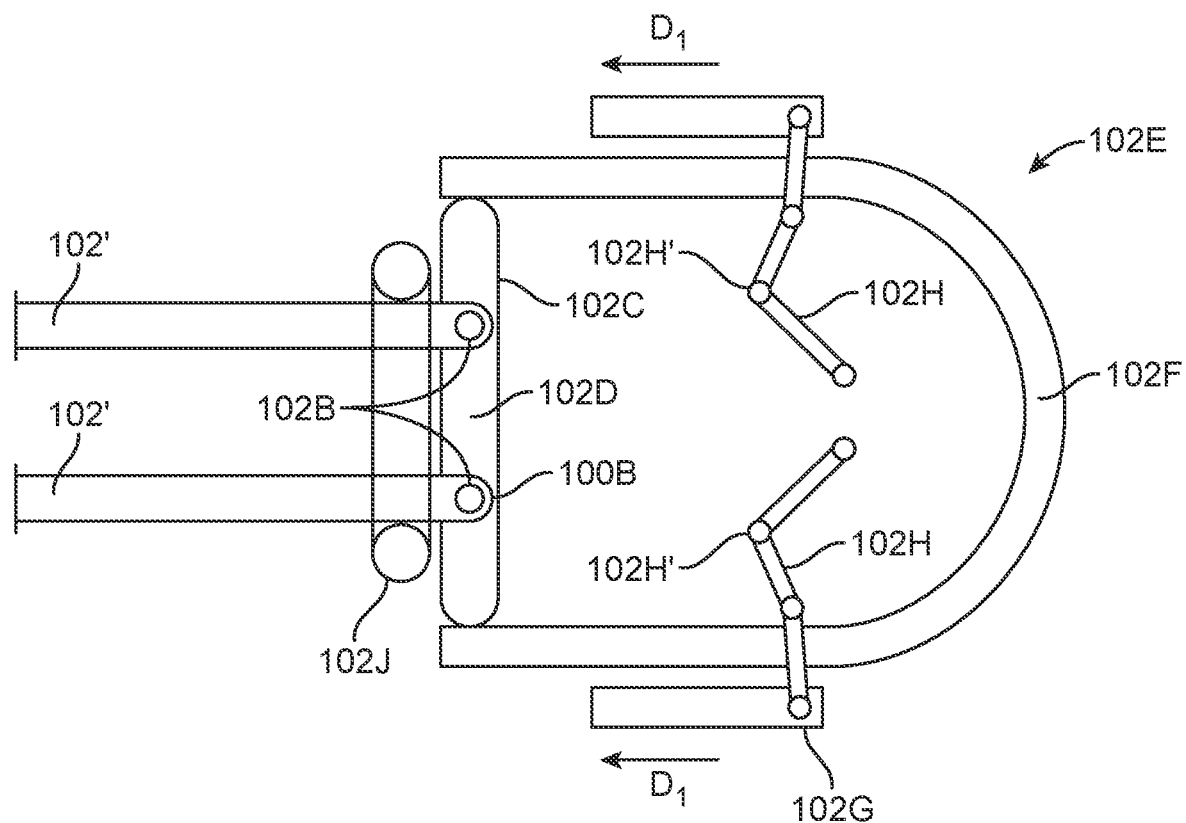

Similarly, in some embodiments, the application requirements may dictate to have a reduced closing force or low-pressure areas. One exemplary embodiment to enable this requirement is illustrated in FIG. 22 through FIG. 24. As depicted in FIG. 22, the base strip segments 102' may be disjointed at distal end 100B. The base strip segments 102', adjacent the distal end 100B, may be provided with hinge pins 102B. The hinge pins 102B may be configured for fitment into a distal bracket 102C. The distal bracket 102C, in accordance with one embodiment, may define a slot 102D within which the hinge pins 102B may be accommodated.

In an embodiment, the distal bracket 102C may be a part of a distal assembly 102E that includes a U-shaped inner tube 102F, and an outer tube 102G placed around both ends of the U-shaped inner tube 102F. The distal assembly 102E further comprises a pair of pivoted links 102H configured in the space defined between the U-shaped inner tube 102F and the distal bracket 102C. The pair of pivoted links 102H are configured to pivot about pivot points 102H'. The distal assembly 102E further comprises actuation linkages 102I coupled to the pair of pivoted links 102H for facilitating the movement of the pair of pivoted links 102H about the pivot points 102H'. The actuation linkages 102I may be coupled to and controlled via the manipulator head 200. The distal assembly further comprises an elastic band 102J placed on the ends of the U-shaped inner tube 102F. In an embodiment, the elastic band 102J may be a silastic band.

The operation of the distal assembly 102E is hereinafter described with reference to FIG. 22 through FIG. 24. The addition of the distal assembly 102E to the occlusion clip 100 provides a configuration of the occlusion clip 100 that has reduced closing force or low-pressure areas, as may be required for certain procedures. As mentioned previously, the base strip segments 102' may be disjointed at distal end 100B, and hinge pins 102B may be configured on the operative ends of the aforementioned base strip segments 102'. When the clip is closed, the base strip segments 102' become parallel to each other, and the hinge pins 102B that were previously placed substantially centrally in the slot 102D may move further apart, as seen in FIG. 23. The further apart the base strip segments 102' are, the less closing force they apply when the occlusion clip 100 is closed. The closing force of the occlusion clip having the distal assembly 102C may be controlled via a precise selection of the elastic band 102J, as per the application requirements. More specifically, the elastic band 102J is applied to the ends of the base strip segments 102' for holding them together in a closed configuration.

The application of the elastic band 102J on the base strip segments 102' is facilitated by the outer tube 102G. The outer tube 102G is moved in the first direction "D1", as shown in FIG. 23 to push the elastic band 102J for application on the base strip segments 102', as shown in FIG. 24. The movement of the outer tube 102G is facilitated by the pair of pivoted links 102H, which in turn are controlled by the actuation linkages 102I. In one embodiment, the actuation linkages 102I may be flexible links extending along the length of the base strip, and the control of which is accessible to the user via the manipulator head 200. The user may push the actuation linkages in a second direction "D2" for facilitating the pivoting movement of the pair of pivoted links 102H about the pivot points 102H', thereby pushing the outer tube 102G in the first direction "D1" and facilitating the application of the elastic band 102J on the base strip segments 102'.

Example embodiments according to at least some aspects of the present disclosure may be configured for use with any desired occlusion devices, including those disclosed in the patent references incorporated by reference herein. Example embodiments according to at least some aspects of the present disclosure may be utilized in connection with surgical procedures, such as occlusion procedures, involving any occludable structure in a patient's body.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure is not limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. An occlusion clip comprising:
   a resilient base strip including a plurality of base strip segments defining a hexagonal profile that represents an open state of the occlusion clip, wherein the vertices of the hexagonal profile are defined by live hinges formed due to a resilient nature of the base strip;
   a plurality of housing segments, wherein one housing segment is provided on each of the base strip segments;
   a pair of core elements, where each core element is disposed and extends within the plurality of housing segments defining a half of the hexagonal profile, the core element is configured for linear movement within the housing segments; and
   an actuator cable extending from each of the core elements, wherein in an actuated state, the core element is pulled via the actuator cable, and the pulling facilitates relative movement between the housing segments and the core elements causing the core element to straighten out the live hinges to make the housing segments collinear, thereby defining a closed configuration of the occlusion clip.

2. The occlusion clip according to claim 1, wherein the base strip and the core elements are made of a resilient material.

3. The occlusion clip according to claim 1, wherein each of the core elements includes a base and a plurality of tabs configured on the base, wherein the plurality of tabs has a shape complementary to a shape of an inner periphery of the housing segments, wherein the housing segments have a hollow configuration.

4. The occlusion clip according to claim 3, wherein plurality of tabs and the inner periphery of the housing segments define a trapezoidal shape such that the core element is allowed guided movement within the housing segments by virtue of the plurality of tabs.

5. The occlusion clip according to claim 3, wherein a first tab of the plurality of tabs is configured to receive the actuator cable securely until the actuator cable is pulled out of the occlusion clip subsequent to the closing of the occlusion clip.

6. The occlusion clip according to claim 5, wherein the first tab is defined by a rigid section and a winged section.

7. The occlusion clip according to claim 6, wherein the winged section comprises a pair of wings configured for extending hingedly and resiliently from laterally opposite ends of rigid section.

8. The occlusion clip according to claim 7, wherein the winged section, including a base of the winged section and the pair of wings of the winged section, define a receiving socket in a closed state of the pair of wings for securely receiving a ball of the actuator cable that facilitates the pulling action of the core elements.

9. The occlusion clip according to claim 8, wherein the ball of the actuator cable is configured to be released from the receiving socket subsequent to an opening of the pair of wings via hinged extension thereof.

10. The occlusion clip according to claim 9, wherein the first tab is housed within a first housing segment of the plurality of housing segments, the first tab including a locking protrusion for facilitating linear movement of the first tab guided in a keyway defined on an inner operative top surface of the first housing segment, wherein the keyway is defined between a pair of spaced apart notches, wherein:
   a first notch is a back out preventer notch that allows abutment of the locking protrusion formed on the first tab for maintaining a position of the core element within the plurality of housing segments when the occlusion clip is in its open state;
   a second notch spaced apart from the first notch and having a shape complementary to that of the locking protrusion, the second notch configured to allow abutment of the locking protrusion thereon; and
   wherein a distance traveled by the first tab between the first notch and the second notch represents a first stage of a closure procedure of the occlusion clip, wherein in the first stage, the occlusion clip is openable subsequent to being closed by maneuvering the actuator cables to linearly move the core element backwards and forwards between the first notch and the second notch.

11. The occlusion clip according to claim 10, further comprising a third notch spaced apart from the second notch, wherein a distance traveled by the first tab between the second notch and the third notch represents a second stage of the closure procedure of the occlusion clip.

12. The occlusion clip according to claim 9, wherein the first housing segment includes a locking cavity configured between the third notch and an operative end of the first housing segment for accommodating therein the spread opened pair of wings after the first tab is pulled beyond the second notch.

13. The occlusion clip according to claim 1, further comprising a clip opener for reopening the occlusion clip after the occlusion clip is closed, wherein the clip opener comprises:
   a spring coupled to a rear end of a tab formed on the core element; and
   a block coupled to the free end of the spring, wherein the tab and the spring are configured to be accommodated inside the slot of the housing segment, and the block protrudes out of the housing segment, wherein the block is configured to be actuated and snap fit into the slot of the housing segment, thereby causing the live hinges of the base strip to bend and change the state of the occlusion clip from the closed state to the open state.

14. The occlusion clip according to claim 13, wherein resilient barrier is configured to be accommodated in slots configured on the housing segments, when the occlusion clip is in the closed state and the housing segments are collinear.

15. The occlusion clip according to claim 13, wherein the resilient barrier is one of a resilient sheet and a plurality of spaced apart bands.

16. The occlusion clip according to claim 1, further comprises a resilient barrier disposed operatively between adjacent housing segments, wherein the resilient barrier prevents an entry of surrounding tissue in a pinch zone formed between the housing segments in the open state of the occlusion clip.

17. The occlusion clip according to claim 1, further comprising a distal end assembly configured on a distal end of the occlusion clip, the distal end assembly comprising:
   hinge pins configured on operative ends of base strip segments disjointed at the distal end;
   a distal bracket defining a slot, wherein the hinge pins are accommodated and moveable within the slot;
   a U-shaped inner tube, wherein the distal bracket is configured between operative ends of the U-shaped inner tube;

an outer tube disposed over the U-shaped inner tube; and an elastic band disposed over the operative ends of the U-shaped inner tube adjacent the outer tube;

a pair of pivoted links configured between the operative ends of the U-shaped inner tube and coupled to the outer tube for facilitating the movement of the outer tube in a first direction; and actuation linkages to the pair of pivoted links, wherein the movement of the actuation linkages in a second direction facilitates the movement of the pivoted links and the outer tube in the first direction.

18. The occlusion clip according to claim 17, wherein the movement of the outer tube in the first direction facilitates the pushing and application of the elastic band onto the base strip segments containing the hinge pins.

19. The occlusion clip according to claim 17, wherein the elastic band is a silastic band.

\* \* \* \* \*